(12) United States Patent
Pykett et al.

(10) Patent No.: US 7,067,316 B2
(45) Date of Patent: *Jun. 27, 2006

(54) METHODS AND DEVICES FOR THE LONG-TERM CULTURE OF HEMATOPOIETIC PROGENITOR CELLS

(75) Inventors: Mark J. Pykett, Boxford, MA (US); Michael Rosenzweig, Boston, MA (US); Richard B. Kaplan, Beverly Hills, CA (US)

(73) Assignee: Cytomatrix, LLC, Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/705,720

(22) Filed: Nov. 10, 2003

(65) Prior Publication Data

US 2005/0079609 A1    Apr. 14, 2005

Related U.S. Application Data

(60) Continuation of application No. 10/143,540, filed on May 10, 2002, now Pat. No. 6,645,489, which is a division of application No. 09/509,379, filed as application No. PCT/US98/20123 on Sep. 25, 1998, now Pat. No. 6,440,734.

(60) Provisional application No. 60/059,954, filed on Sep. 25, 1997.

(51) Int. Cl.
    C12N 5/02    (2006.01)
(52) U.S. Cl. ........................... 435/402; 435/372
(58) Field of Classification Search ............... 424/93.7; 435/372, 402, 289.1
    See application file for complete search history.

(56) References Cited

U.S. PATENT DOCUMENTS

| | | | |
|---|---|---|---|
| 5,061,620 A | 10/1991 | Tsukamoto et al. | |
| 5,282,861 A | 2/1994 | Kaplan | |
| 5,443,950 A | 8/1995 | Naughton et al. | |
| 5,510,262 A | 4/1996 | Stephanopoulos | |
| 5,580,781 A | 12/1996 | Naughton et al. | |
| 5,635,387 A | 6/1997 | Fei et al. | |
| 5,677,139 A | 10/1997 | Johnson et al. | |
| 6,440,734 B1* | 8/2002 | Pykett et al. | 435/372 |
| 6,548,299 B1 | 4/2003 | Pykett et al. | |
| 6,645,489 B1* | 11/2003 | Pykett et al. | 424/93.7 |
| 2003/0096404 A1 | 5/2003 | Pykett et al. | |

FOREIGN PATENT DOCUMENTS

| | | |
|---|---|---|
| EP | 0 241 578 A | 10/1987 |
| EP | 0 358 506 | 3/1990 |
| EP | 0 560 279 A | 9/1993 |
| WO | WO 90/15877 A | 12/1990 |
| WO | WO 96/33265 | 10/1996 |
| WO | WO 97/33978 A | 9/1997 |
| WO | WO 99/15629 | 4/1999 |
| WO | WO 00/27999 | 5/2000 |
| WO | WO 01/11011 A2 | 2/2001 |
| WO | WO 01/21760 | 3/2001 |
| WO | WO 01/21766 | 3/2001 |
| WO | WO 03/100010 | 12/2003 |

OTHER PUBLICATIONS

Anderson, et al., "MHC class II-positive epithelium and mesenchyme cells are both required for T-cell development in the thymus", *Nature*, 362, pp. 70-73 (1993).

Bagley, et al., "Extended culture of multipotent hematopoietic progenitors without cytokine augmentation in a novel three-dimensional device", *Experimental Hematology*, 27(3), pp. 496-504 (1999).

Bagley, et al., "Long-term three dimensional hematopoietic stem cell culture", *Amer. Chem. Soc.*, 126(Jan. 2003). Abstract Only.

Bobyn, et al., "Characteristics of bone ingrowth and interface mechanics of a new porous tantalum biomaterial", *Journal of Bone & Joint Surgery (Br.)*, 81-B(5), pp. 907-914 (1999).

Boyd, et al. "The thymic microenvironment", *Immunology Today*, 14(9), pp. 445-459 (1993).

Clay, et al., "Potential use of T cell receptor genes to modify hematopoietic stem cells for the gene therapy of cancer", *Pathology Oncology Research*, 5(1), pp. 3-15 (1999).

Freedman, et al., "Generation of human T lymphocytes from bone marrow CD34+ cells in vitro", Nature Medicine, 2(1), pp. 46-51 (1996).

Gardner, et al., "T-lymphopoietic capacity of cord blood-derived CD34+ progenitor cells", *Experimental Hematology*, 26, pp. 991-999 (1998).

Naughton, et al., "Three-dimensional bone marrow cell and tissue culture system", *Biotech. Adv.*, 15(2) (1997). Abstract Only.

Naughton, et al., "Three-dimensional culture system for the growth of hematopoietic cells", *Prog. Clin. Biol. Res.*, 333, pp. 435-445, (1990).

(Continued)

Primary Examiner—James Ketter
(74) Attorney, Agent, or Firm—Wolf, Greenfield & Sacks, P.C.

(57) ABSTRACT

The invention pertains to methods and devices for the long term, in vitroculture of hematopoietic progenitor cells in the absence of exogenously added hematopoietic growth factors, improved methods for the introduction of foreign genetic material into cells of hematopoietic origin, and to apparatus for performing these methods. The hematopoietic progenitor cells are cultured on a three-dimensional porous biomaterial. The three-dimensional porous biomaterial enhances hematopoietic progenitor cell survival and leads to an expansion of progenitor cell numbers and/or functionality, while maintaining progenitor cell pluripotency in the absence of exogenous growth factors. In addition, the three-dimensional porous biomaterial supports high level transduction on cells cultured upon such environment.

20 Claims, 7 Drawing Sheets

OTHER PUBLICATIONS

Pawelec, et al., "Extrathymic T cell differentiation in vitro from human CD34+ stem cells", *Journal of Leukocyte Biology*, 64, pp. 733-739 (1998).

Porter, et al., "A tissue of T cells", *Nature Biotechnology*, 18, pp. 714-715 (2000).

Poznansky, et al., "Efficient generation of human T cells from a tissue-engineered thymic organoid", *Nature Biotechnology*, 18, pp. 729-734 (2000).

Rosenzweig, et al., "T-cell differentiation of human and non-human primate CD34+ hematopoietic progenitor cells using porcine thymic stroma", *Xenotransplantation*, 8, pp. 185-192 (2001).

Rosenzweig, et al., "Enhanced maintenance and retroviral transduction of primitive hematopoietic progenitor cells using a novel three-dimensional culture system", *Gene Therapy*, 4(9), pp. 928-936 (1997).

Rosenzweig, et al., "In vitro T lymphopoiesis of human and rhesus CD34+ progenitor cells", *Blood*, 87(10), pp. 4040-4048 (1996).

Rosenzweig, et al., "In vitro T lymphopoiesis: A model system for stem cell gene therapy for AIDS", *Journal of Medical Primatology*, 25, pp. 192-200 (1996).

Stackpool, GJ, et al., "Bone ingrowth characteristics of porous tantalum: a new material for orthopaedic implants", *Combined Orthopaedic Research Societies Meeting, Nov. 6-8*, 1995, San Diego, CA, Abstract Book p. 45.

Turner, TM, et al., "Evaluation of tantalum foam, a novel porous material, for bone ingrowth fixation using a canine model", 21st *Annual Meeting of the Society for Biomaterials, Mar. 18-22*, San Francisco, CA, Abstract Book, p. 125.

Van Ewijk, "T-cell differentiation is influenced by thymic microenvironments", *Annual Review of Immunology*, 9, pp. 591-615 (1991).

Van Vliet, et al., "Stromal cell types in the developing thymus of the normal and nude mouse embryo", *European Journal of Immunology*, 15, pp. 675-681 (1985).

Wang, et al, "Multilineal hematopoiesis in a three-dimensional murine long-term bone marrow culture", *Experimental Hematology*, pp. 26-32, (1995).

Banu et al., Cytokine-augmented culture of haematopoietic progenitor cells in a novel three-dimensional cell growth matrix. Cytokine. Mar. 21, 2001;13(6):349-58.

\* cited by examiner

METHODS AND DEVICES FOR THE LONG-TERM CULTURE OF HEMATOPOIETIC PROGENITOR CELLS

RELATED APPLICATIONS

This application is continuation of application Ser. No. 10/143,540, filed on May 10, 2002, now issued as U.S. Pat. No. 6,645,489 which is a divisional of application Ser. No. 09/509,379, filed on Jun. 7, 2000, entitled METHODS AND DEVICES FOR THE LONG-TERM CULTURE OF HEMATOPOIETIC PROGENITOR CELLS, now issued as U.S. Pat. No. 6,440,734, which is the National Stage filing of PCT/US98/20123 application filed on Sep. 25, 1998, and which in turn claims priority from U.S. Provisional application Ser. No. 60/059,954 filed on Sep. 25, 1997. The contents of the foregoing applications are hereby expressly incorporated by reference.

GOVERNMENT SUPPORT

This work was funded in part under contract DAAH01-97-C-R121 from the U.S. Army Aviation and Missile Command. Accordingly, the United States Government may have certain rights to this invention.

FIELD OF THE INVENTION

This invention relates generally to hematopoietic cells, and more specifically to methods and devices for long-term in vitro culturing of hematopoietic progenitor cells, as well as methods for the introduction of exogenous genetic material into cells of hematopoietic origin.

BACKGROUND OF THE INVENTION

The circulating blood cells, such as erythrocytes, leukocytes, platelets and lymphocytes, are the products of the terminal differentiation of recognizable precursors. In fetal life, hematopoiesis occurs throughout the reticular endothelial system. In the normal adult, terminal differentiation of the recognizable precursors occurs exclusively in the marrow cavities of the axial skeleton, with some extension into the proximal femora and humeri. These precursor cells, in turn, derive from very immature cells, called progenitors, which are assayed by their development into contiguous colonies of mature blood cells in 1–3 week cultures in semi-solid media, such as methylcellulose.

There have been reports of the isolation and purification of hematopoietic progenitor cells (see, e.g., U.S. Pat. No. 5,061,620 as representative), but such methods have not allowed for the long-term culture of such cells that maintain their viability and pluripotency.

Studies of the murine hematopoietic system in the murine bone marrow have resulted in a detailed understanding of the murine system. In addition, retroviral gene transfer into cultured mouse bone marrow cells has been made possible. While it has been possible to transfer retroviral genes into cultured mouse bone marrow cells, the efficiency of gene transfer into human bone marrow cells has been disappointing to date, which may reflect the fact that human long-term bone marrow cultures have been limited both in their longevity and more importantly in their ability to maintain hematopoietic progenitor cell survival and pluripotentiality over time.

Human bone marrow cultures initially were found to have a limited hematopoietic potential, producing decreasing numbers of hematopoietic progenitor and mature blood cells, with cell production ceasing by six to eight weeks. Subsequent modifications of the original system resulted only in minor improvements. This has been largely attributed to the dependence of the hematopoietic progenitor cells upon environmental influences such essential growth factors (hematopoietic growth factors and cytokines) found in vivo. In addition to these factors, interactions with cell surface molecules and extracellular matrix may be important for hematopoietic progenitor cell survival and proliferation. Previous efforts to advance in vitro proliferation and differentiation of hematopoietic progenitor cells, examined the effects of cytokines in various substrates, including pre-seeded stroma and fibronectin. The addition of exogenous growth factors to the culture environment, particularly IL-3 (Interleukin-3) and GM-CSF (Granulocyte Macrophage-Colony Stimulating, Factor), may lead to selective expansion of specific lineages. These findings suggest that addition of exogenous growth factors into hematopoietic progenitor cell cultures may adversely affect the multipotency of primitive hematopoietic progenitor cells by causing them to differentiate and thus depleting the immature hematopoietic progenitor population.

Alternative approaches have used irradiated bone marrow stroma to seed hematopoietic progenitor cells and have been shown to maintain these cells in long-term culture initiating cells (LTCICs) and to increase transduction of hematopoietic progenitor cells and LTCICs by retroviral vectors. However, questions have been raised about the risks of infection and immune reaction to transplantation of non-autologous bone marrow. Fibronectin, a cellular stromal component, reduces this risk of infection and immune mediated response while enhancing retroviral transduction. However, fibronectin alone may not be sufficient to maintain primitive hematopoietic progenitor cells in vitro.

The hypothesis that the three-dimensional micro-environment of the bone marrow plays a role in maintaining hematopoietic stem cell viability and pluripotency has led to investigating structures which mimic this topography. Three-dimensional polymer devices (e.g., nylon mesh) have been shown to support hematopoietic progenitor cell survival, proliferation and multilineage differentiation, but require the presence of growth factors. Such factors can be added exogenously, or supplied via secreting stromal cells which are co-cultured with the progenitor cells, or through the addition of stromal cell conditioned medium.

Hematopoietic progenitor cell expansion for bone marrow transplantation is a potential application of human long-term bone marrow cultures. Human autologous and allogeneic bone marrow transplantation are currently used as therapies for diseases such as leukemia, lymphoma, and other life-threatening diseases. For these procedures, however, a large amount of donor bone marrow must be removed to ensure that there are enough cells for engraftment.

An approach providing hematopoietic progenitor cell expansion would reduce the need for large bone marrow donation and would make possible obtaining a small marrow donation and then expanding the number of progenitor cells in vitro before infusion into the recipient. Also, it is known that a small number of hematopoietic progenitor cells circulate in the blood stream. If these cells could be selected and expanded, then it would be possible to obtain the required number of hematopoietic progenitor cells for transplantation from peripheral blood and eliminate the need for bone marrow donation.

Hematopoietic progenitor cell expansion would also be useful as a supplemental treatment to chemotherapy and is another application for human long-term bone marrow cultures. Most chemotherapy agents act by killing all cells going through cell division. Bone marrow is one of the most prolific tissues in the body and is therefore often the organ that is initially damaged by chemotherapy drugs. The result is that blood cell production is rapidly destroyed during chemotherapy treatment, and chemotherapy must be terminated to allow the hematopoietic system to replenish the blood cell supplies before a patient is re-treated with chemotherapy.

A successful approach providing hematopoietic progenitor cell expansion would greatly facilitate the production of a large number of further differentiated precursor cells of a specific lineage, and in turn provide a larger number of differentiated hematopoietic cells with a wide variety of applications, including blood transfusions.

Gene therapy is a rapidly growing field in medicine with an enormous clinical potential. Traditionally, gene therapy has been defined as a procedure in which an exogenous gene is introduced into the cells of a patient in order to correct an inborn genetic error. Research in gene therapy has been ongoing for several years in several types of cells in vitro and in animal studies, and more recently a number of clinical trials have been initiated.

The human hematopoietic system is an ideal choice for gene therapy in that hematopoietic stem cells are readily accessible for treatment (bone marrow or peripheral blood harvest) and they are believed to possess unlimited self-renewal capabilities (incurring lifetime therapy), and upon reinfusion, can expand and repopulate the marrow. Unfortunately, achieving therapeutic levels of gene transfer into stem cells has yet to be accomplished in humans. The problem which remains to be addressed for successful human gene therapy is the ability to insert the desired therapeutic gene into the chosen cells in a quantity such that it will be beneficial to the patient. To date, methods for the efficient introduction of exogenous genetic material into human hematopoietic stem cells have been limited.

There exists a need to influence favorably hematopoietic progenitor cell viability and pluripotency under long-term culture in vitro.

There exists a need to provide large numbers of differentiated hematopoietic cells.

There also exists the need to improve the efficiency of exogenous genetic material transfer into hematopoietic progenitor cells.

An object of the invention is to provide methods and devices that extend the in vitro viability of hematopoietic stem cells while maintaining the hematopoietic progenitor cell properties of self-renewal and pluripotency.

Another object of the invention is to provide methods and devices for the controlled production in large numbers of specific lineages of progenitor cells and their more differentiated hematopoietic cells.

Yet another object of the invention is to provide improved methods for gene transfer and transduction into cells of hematopoietic origin and hematopoietic progenitor cells in particular. These and other objects of the invention will be described in greater detail below.

SUMMARY OF THE INVENTION

The invention, in one important part, involves improved methods for culturing hematopoietic progenitor cells, which methods can, for example, increase the period over which an amount of hematopoietic progenitor cells can be cultured. Thus, one aspect of the invention is improved preservation of a culture of hematopoietic progenitor cells. Another aspect is an improvement in the number of progeny that can be obtained from a sample of hematopoietic progenitor cells. Still another aspect of the invention is an improvement in the number of differentiated progeny blood cells that can be obtained from a sample of hematopoietic progenitor cells.

Surprisingly, according to the invention, it has been discovered that hematopoietic progenitor cells can be cultured without exogenous growth agents for extended periods of time, thereby increasing the supply of hematopoietic progenitor cells and inhibiting the induction of differentiation and/or the loss of progenitor cells during culture. Thus, the present invention permits the culture of hematopoietic progenitor cells in vitro for more than 5 weeks, and even more than 6, 7 or 8 weeks, without adding hematopoietic growth factors, inoculated stromal cells or stromal cell conditioned medium. This is achieved, simply, by culturing the hematopoietic progenitor cells in a porous solid scaffold.

According to one aspect of the invention, a method for in vitro culture of hematopoietic progenitor cells is provided. An amount of hematopoietic progenitor cells is introduced to a porous, solid matrix having interconnected pores of a pore size sufficient to permit the cells to grow throughout the matrix. The cells are cultured upon and within the matrix in an environment that is free of inoculated stromal cells, stromal cell conditioned medium, and exogenously added hematopoietic growth factors that promote hematopoietic cell differentiation, other than serum. The porous matrix can be one that is an open cell porous matrix having a percent open space of at least 50%, and preferably at least 75%. In one embodiment the porous solid matrix has pores defined by interconnecting ligaments having a diameter at midpoint, on average, of less than 150 µm. Preferably the porous solid matrix is a metal-coated reticulated open cell foam of carbon containing material, the metal coating being selected from the group consisting of tantalum, titanium, platinum (including other metals of the platinum group), niobium, hafnium, tungsten, and combinations thereof. In preferred embodiments, whether the porous solid matrix is metal-coated or not, the matrix is coated with a biological agent selected from the group consisting of collagens, fibronectins, laminins, integrins, angiogenic factors, anti-inflammatory factors, glycosaminoglycans, vitrogen, antibodies and fragments thereof, functional equivalents of these factors, and combinations thereof. Most preferably the metal coating is tantalum coated with a biological agent. In certain other embodiments the porous solid matrix having seeded hematopoietic progenitor cells and their progeny is impregnated with a gelatinous agent that occupies pores of the matrix.

The preferred embodiments of the invention are solid, unitary macrostructures, i.e. not beads or packed beads. They also involve nonbiodegradable materials.

In other embodiments, before the introducing step, the hematopoietic progenitor cells are obtained from a blood product. Preferably the blood product is unfractionated bone marrow. In still other embodiments, the method further includes the step of harvesting hematopoietic cells. Preferably, there is a first harvesting after a first culturing period and at least one additional harvesting after at least one additional culturing period. The harvested cells then are cultured in at least one of an exogenously added agent selected from the group consisting of a hematopoietic growth factor that promotes hematopoietic cell maintenance, expansion and/or differentiation, inoculated stromal cells, and stromal cell conditioned medium.

According to any of the foregoing embodiments, the method of the invention can include, in said first culturing step, culturing the cells in an environment that is free of hematopoietic progenitor cell survival and proliferation factors such as interleukins 3, 6 and 11, stem cell ligand and FLT-3 ligand. As mentioned above, the inventors have discovered, surprisingly, that hematopoietic progenitor cells can be grown for extended periods of time without the addition of any of these agents which typically are added in the prior art in order to prevent the hematopoietic progenitor cells from dying within several weeks. Still another embodiment of the invention is performing the first culturing step in an environment that is free altogether of any exogenously added hematopoietic progenitor cell growth factors, other than serum.

As will be understood, according to the invention, it is possible now to culture hematopoietic progenitor cells for 6, 7 or 8 weeks, and to harvest hematopoietic progenitor cells during this time interval for subsequent exposure to culture conditions containing hematopoietic growth factors that promote hematopoietic cell maintenance, expansion and/or differentiation. Culturing and harvesting over this time period is an independent aspect of the invention.

According to another aspect of the invention, a method is provided for in vitro culture of hematopoietic progenitor cells to produce differentiated cells of hematopoietic origin. In a first culturing step, a first amount of hematopoietic progenitor cells is cultured in an environment that is free of inoculated stromal cells, stromal cell condition medium and exogenously added hematopoietic growth factors that promote hematopoietic cell maintenance, expansion and/or differentiation, other than serum, under conditions and for a period of time to increase the number of cultured hematopoietic progenitor cells relative to said first amount or to increase the functionality of the hematopoietic progenitor cells, thereby producing a second amount of hematopoietic progenitor cells. Then, in a second culturing step, at least a portion of the second amount of cultured hematopoietic progenitor cells is cultured in an environment that includes at least one of an agent selected from the group consisting of a hematopoietic growth factor that promotes hematopoietic cell maintenance, expansion and/or differentiation, inoculated stromal cells and stromal cell conditioned medium, to produce differentiated cells of hematopoietic origin. In one embodiment, the environment is free of hematopoietic growth factors that promote survival and proliferation of hematopoietic progenitor cells such as interleukins 3, 6 and 11, stem cell ligand and FLT-3 ligand. In another embodiment, the environment of the first culturing step is free of any hematopoietic growth factors other than those present as a result of the addition of serum to the nutritive medium. In this aspect of the invention, the method further can comprise a second culturing step which is a plurality of second culturing steps, each comprising culturing only a portion of the second amount of hematopoietic progenitor cells. The method also can involve a harvesting step between the first and second culturing steps, wherein the harvesting step comprises harvesting the at least a portion of the second amount prior to culturing the at least a portion of the second amount in the second culturing step. The harvesting step also can be a plurality of harvesting steps spaced apart in time and, in this instance, the second culturing step can be a plurality of second culturing steps, one for each of the harvesting steps. The preferred source of the hematopoietic progenitor cells and the preferred configuration of the porous solid matrix is as described above.

According to another aspect of the invention, a method is provided for in vitro culture of hematopoietic progenitor cells to produce differentiated cells of hematopoietic origin. In a first culturing step, hematopoietic progenitor cells are cultured in an environment that is free of inoculated stromal cells, stromal cell condition medium and exogenously added hematopoietic growth factors that promote differentiation, other than serum, to generate cultured hematopoietic progenitor cells. A portion of the cultured hematopoietic progenitor cells are harvested intermittently to generate a plurality of intermittently harvested portions of cultured hematopoietic cells. Then, in a plurality of second culturing steps, the plurality of intermittently cultured harvested portions are cultured in an environment that includes at least one agent selected from the group consisting of a hematopoietic growth factor that promotes differentiation, inoculated stromal cells and stromal cell conditioned medium, to produce differentiated cells of hematopoietic origin. In one embodiment, the environment of the first culturing step is free of hematopoietic growth factors that promote survival and proliferation of hematopoietic progenitor cells, such as interleukins 3, 6 and 11, stem cell ligand and FLT-3 ligand. In another embodiment, the environment of the first culturing step is free of any hematopoietic growth factors, other than those present as a result of the addition of serum to the nutritive medium. In this aspect of the invention, the preferred source of hematopoietic progenitor cells and the preferred porous solid matrix are as described above.

According to another aspect of the invention, a method is provided for transducing exogenous genetic material into cells of hematopoietic origin. Hematopoietic cells are cultured in a porous solid matrix having interconnected pores of a pore size sufficient to permit the cells to grow throughout the matrix. The cells are transduced with the exogenous genetic material in situ on and within the matrix. It has been found, surprisingly, that the efficiency of transfer of genetic material when carried out with the cells cultured upon the matrix is unexpectedly increased. The characteristics of various embodiments of the preferred porous solid matrices are as described above. Also, in this embodiment, the hematopoietic cells can be hematopoietic progenitor cells and the cells, whether progenitor or not, can be cultured in environments free of factors that promote differentiation, factors that promote survival and proliferation, any hematopoietic growth factors whatsoever, inoculated stromal cells or stromal cell conditioned media.

According to still another aspect of the invention, an apparatus for culturing cells is provided. The apparatus includes a first cell culture chamber containing a porous solid matrix having interconnected pores of a pore size sufficient to permit cells to grow throughout the matrix. The apparatus also includes a second cell culture chamber. A conduit provides fluid communication between the first and second cell culture chambers. A collection chamber is located between the first and second cell culture chambers, the collection chamber interrupting fluid communication between the first and second cell culture chambers via the conduit. A first inlet valve on one side of the collection chamber is for providing fluid to be received from the first cultured chamber into the collection chamber. An outlet valve on the other side of the collection chamber provides fluid to be received into the second cultured chamber from the collection chamber. Finally, there is a second inlet valve for the collection chamber for introducing a desired fluid into the collection chamber, other than fluid from the first cell culture chamber, whereby fluid may be intermittently removed from the first cell culture chamber and provided to the second cell culture chamber without contamination of the first culture chamber by fluid from the second culture chamber.

According to yet another aspect of the invention, another apparatus for culturing cells is provided. This apparatus includes a first cell culture chamber containing a porous solid matrix having interconnected pores of a pore size sufficient to permit cells to grow throughout the matrix. An inlet valve on the first cell culture chamber is provided for introducing culture medium into the first cell culture chamber. A second cell culture chamber also is provided, the first and second cell culture chambers being in fluid communication with one another via a conduit. A valve on the conduit is provided for controlling fluid flow between the first and second cell culture chambers.

In either of the foregoing apparatus, the second cell culture chamber can be provided with a porous solid matrix having interconnected pores of a pore size sufficient to permit cells to grow throughout the matrix. Various embodiments are provided, wherein the porous solid matrix has one or more of the preferred characteristics as described above. In addition, the various cell culture chambers can have ports and conduits for sampling material within the cell culture chamber, for augmentation by delivery of various agents to one or the other of the cell culture chambers and for controlling and permitting the continuous flow of medium through either or both of the cell culture chambers.

In yet another aspect of the invention, a solid porous matrix is provided wherein hematopoietic progenitor cells, with or without their progeny, are attached to the solid porous matrix. In some embodiments, stromal cells may also be attached to the matrix. The porous matrix can be one that is an open cell porous matrix having a percent open space of at least 50%, and preferably at least 75%. In one embodiment the porous solid matrix has pores defined by interconnecting ligaments having a diameter at midpoint, on average, of less than 150 µm. Preferably the porous solid matrix is a metal-coated reticulated open cell foam of carbon containing material, the metal coating being selected from the group consisting of tantalum, titanium, platinum (including other metals of the platinum group), niobium, hafnium, tungsten, and combinations thereof. In preferred embodiments, whether the porous solid matrix is metal-coated or not, the matrix is coated with a biological agent selected from the group consisting of collagens, fibronectins, laminins, integrins, angiogenic factors, anti-inflammatory factors, glycosaminoglycans, vitrogen, antibodies and fragments thereof, functional equivalents of these factors, and combinations thereof. Most preferably the metal coating is tantalum coated with a biological agent. In certain other embodiments the porous solid matrix having seeded hematopoietic progenitor cells and their progeny is impregnated with a gelatinous agent that occupies pores of the matrix.

According to another aspect of the invention, a method for in vivo maintenance, expansion and/or differentiation of hematopoietic progenitor cells is provided. The method involves implanting into a subject a porous, solid matrix having pre-seeded hematopoietic progenitor cells and hematopoietic progenitor cell progeny. The porous matrix has interconnected pores of a pore size sufficient to permit the cells to grow throughout the matrix and is an open cell porous matrix having a percent open space of at least 50%, and preferably at least 75%. Various embodiments are provided, wherein the porous solid matrix has one or more of the preferred characteristics as described above. In certain other embodiments, the porous solid matrix further comprises hematopoietic progenitor cells and their progeny which are attached to the matrix by introducing in vitro an amount of hematopoietic progenitor cells into the porous solid matrix, and culturing the hematopoietic progenitor cells in an environment that is free of inoculated stromal cells, stromal cell conditioned medium, and exogenously added hematopoietic growth factors that promote hematopoietic cell maintenance, expansion and/or differentiation, other than serum. In yet other embodiments the porous solid matrix having seeded hematopoietic progenitor cells and their progeny is impregnated with a gelatinous agent that occupies pores of the matrix.

In any of the foregoing embodiments involving hematopoietic cell maintenance, expansion and/or differentiation using a hematopoietic growth factor, the hematopoietic growth factor used is selected from the group consisting of interleukin 3, interleukin 6, interleukin 7, interleukin 11, interleukin 12 stem cell factor, FLK-2 ligand, FLT-2 ligand, Epo, Tpo, GMCSF, GCSF, Oncostatin M, and MCSF.

These and other aspects of the invention are described in greater detail below.

DETAILED DESCRIPTION OF THE INVENTION

Figure 1:
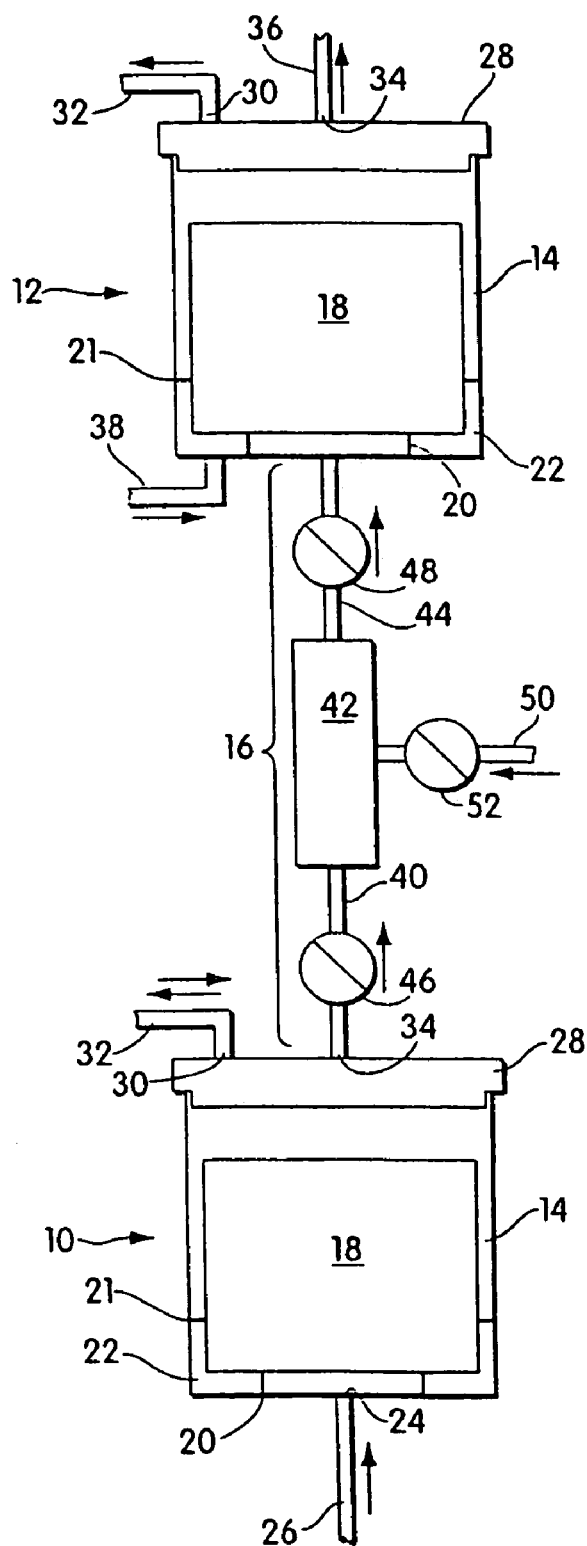
FIG. 1 is a schematic representation of a cell culture apparatus according to the invention.
Figure 2:
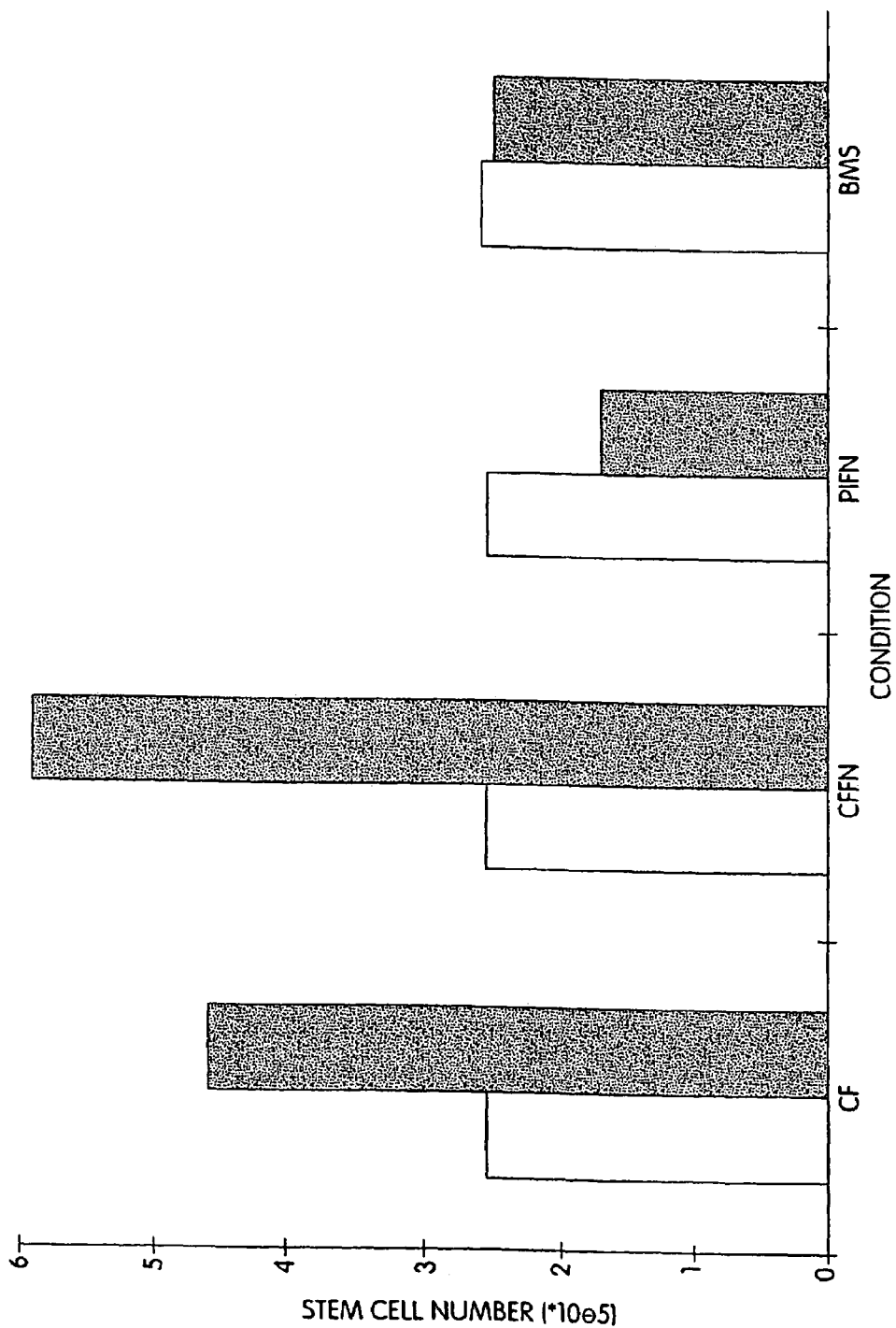
FIG. 2. Survival and expansion of $CD34^+$ HPCs in Cellfoam v. control systems at 1 week.

The invention in one aspect involves culturing hematopoietic progenitor cells in a porous solid matrix without exogenous growth agents.

A porous, solid matrix, is defined as a three-dimensional structure with "sponge-like" continuous pores forming an interconnecting network. The matrix can be rigid or elastic, and it provides a scaffold upon which cells can grow throughout. Its pores are interconnected and provide the continuous network of channels extending through the matrix and also permit the flow of nutrients throughout. A preferred matrix is an open cell foam matrix having a percent open space of at least 50% and preferably 75%. Thus, it is preferred that the open space comprise the majority of the matrix. This is believed to maximize cell migration, cell-cell contact, space for cell growth and accessibility to nutrients. It is preferred that the porous matrix be formed of a reticulated matrix of ligaments which at their center point are less than 150 µm in diameter, preferably 60 µm, whereby a cell can reside on or interact with a portion of the ligament. Preferably, the average pore diameter is on the order of 300 μm, which resembles cancellous bone. Suitable matrices can be obtained using a number of different methods. Examples of such methods include solvent casting or extraction of polymers, track etching of a variety of materials, foaming of a polymer, the replamineform process for hydroxyapatite, and other methodologies well known to those of ordinary skill in the art. The materials employed can be natural or synthetic, including biological materials such as proteins, hyaluronic acids, synthetic polymers such as polyvinyl pyrolidones, polymethylmethacrylate, methyl cellulose, polystyrene, polypropylene, polyurethane, ceramics such as tricalcium phosphate, calcium aluminate, calcium hydroxyapatite and ceramic-reinforced or coated polymers. If the starting material for the scaffold is not metal, a metal coating can be applied to the three-dimensional matrix. Metal coatings provide further structural support and/or cell growth and adhesive properties to the matrix. Preferred metals used as coatings comprise tantalum, titanium, platinum and metals in the same element group as platinum, niobium, hafnium, tungsten, and combinations of alloys thereof. Coating methods for metals include a process such as CVD (Chemical Vapor Deposition). The preferred matrix, refered to herein throughout as Cellfoam, is described in detail in U.S. Pat. No. 5,282,861, and is incorporated herein by reference. More specifically, the preferred matrix is a reticulated open cell substrate formed by a lightweight, substantially rigid foam of carbon-containing material having open spaces defined by an interconnecting network, wherein said foam material has interconnected continuous channels, and a thin film of metallic material deposited onto the reticulated open cell substrate and covering substantially all of the interconnecting network to form a composite porous biocompatible material creating a porous microstructure similar to that of natural cancellous bone.

Additionally, such matrices can be coated with biological agents which can promote cell adhesion for the cultured hematopoietic cells, allowing for improved migration, growth and proliferation. Moreover, when these matrices are used for the in vivo maintenance, expansion and/or differentiation of hematopoietic progenitor cells (i.e., when the matrices with the cells are implanted into a subject, —see also discussion below), biological agents that promote angiogenesis (vascularization) and biological agents that prevent/reduce inflammation may also be used for coating of the matrices. Preferred biological agents comprise collagens, fibronectins, laminins, integrins, angiogenic factors, anti-inflammatory factors, glycosaminoglycans, vitrogen, antibodies and fragments thereof, functional equivalents of these agents, and combinations thereof.

Angiogenic factors include platelet derived growth factor (PDGF), vascular endothelial growth factor (VEGF), basic fibroblast growth factor (bFGF), bFGF-2, leptins, plasminogen activators (tPA, uPA), angiopoietins, lipoprotein A, transforming growth factor-β, bradykinin, angiogenic oligosaccharides (e.g., hyaluronan, heparan sulphate), thrombospondin, hepatocyte growth factor (also known as scatter factor) and members of the CXC chemokine receptor family. Anti-inflammatory factors comprise steroidal and non-steroidal compounds and examples include: Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol; Pivalate; Tolmetin; Tolmetin Sodium; Triclonide; Triflumidate; Zidometacin; Zomepirac Sodium.

In certain embodiments of the invention the porous solid matrix having seeded hematopoietic progenitor cells, with or without their progeny, is impregnated with a gelatinous agent that occupies pores of the matrix. By "seeded" it is meant that the hematopoietic progenitor cells, with or without their progeny, are seeded prior to, substantially at the same time as, or following impregnation (or infiltration) with a gelatinous agent. For example, the cells may be mixed with the gelatinous agent and seeded at the same time as the the impregnation of the matrix with the agent. In some embodiments, the hematopoietic progenitor cells, with or without their progeny, are pre-seeded onto the porous solid matrix. According to the invention, an amount of the cells is introduced in vitro into the porous solid matrix, and cultured in an environment that is free of inoculated stromal cells, stromal cell conditioned medium, and exogenously added hematopoietic growth factors that promote hematopoietic cell maintenance, expansion and/or differentiation, other than serum.

"Impregnation" with a gelatinous agent serves as to contain the cells within the matrix, and also to help maintain and/or enhance cell attachment onto the matrix. The "gelatinous" agent may be one that can be maintained in a fluid state initially, and after its application into the matrix, be gelatinized in situ in the matrix. Such gelatinization may to occur in a number of different ways, including altering the agent's temperature, irradiating the agent with an energy source (e.g., light), etc. The agent may exist in a continuum from a fluid state to a semi-solid (gelatinous) state to a solid state. An agent's final state and gelatinization will always depend upon the particular "gelatinous" agent used and its individual properties. A preferred "gelatinous" agent is characterized also by its structural porosity, necessary for allowing the nutrients of the growth media to reach the cells throughout the matrix. Exemplary "gelatinous" agents include cellulosic polysaccharides (such as cellulose, hemicellulose, methylcellulose, and the like), agar, agarose, albumin, algal mucin, mucin, mucilage, collagens, glycosaminoglycans, and proteoglycans (including their sulphated forms). In certain embodiments, the gelatinous agent may impregnate the matrix completely, in some embodiments partially, and in other embodiments minimally, serving only as a coating of the outer surfaces of the matrix. The extent of the impregnation will largely depend upon the physical characteristics of the "gelatinous" agent of choice. In preferred embodiments the "gelatinous" agent is methylcellulose and the impregnation is complete.

The cells cultured according to the methods of the invention are hematopoietic progenitor cells. "Hematopoietic progenitor cells" as used herein refers to immature blood cells having the capacity to self-renew and to differentiate into the more mature blood cells (also described herein as "progeny") comprising granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g., monocytes, macrophages). It is known in the art that such cells may or may not include $CD34^+$ cells. $CD34^+$ cells are immature cells present in the "blood products" described below, express the CD34 cell surface marker, and are believed to include a subpopulation of cells with the "progenitor cell" properties defined above.

The hematopoietic progenitor cells can be obtained from blood products. A "blood product" as used in the present invention defines a product obtained from the body or an organ of the body containing cells of hematopoietic origin. Such sources include unfractionated bone marrow, umbilical cord, peripheral blood, liver, thymus, lymph and spleen. It will be apparent to those of ordinary skill in the art that all of the aforementioned crude or unfractionated blood products can be enriched for cells having "hematopoietic progenitor cell" characteristics in a number of ways. For example, the blood product can be depleted from the more differentiated progeny. The more mature, differentiated cells can be selected against, via cell surface molecules they express. Additionally, the blood product can be fractionated selecting for $CD34^+$ cells. As mentioned earlier, $CD34^+$ cells are thought in the art to include a subpopulation of cells capable of self-renewal and pluripotentiality. Such selection can be accomplished using, for example, commercially available magnetic anti-CD34 beads (Dynal, Lake Success, N.Y.). Unfractionated blood products can be obtained directly from a donor or retrieved from cryopreservative storage.

Employing the culture conditions described in greater detail below, it is possible according to the invention to preserve hematopoietic progenitor cells and to stimulate the expansion of hematopoietic progenitor cell number and/or colony forming unit potential. Once expanded, the cells, for example, can be returned to the body to supplement, replenish, etc. a patient's hematopoietic progenitor cell population. This might be appropriate, for example, after an individual has undergone chemotherapy. There are certain genetic conditions wherein hematopoietic progenitor cell numbers are decreased, and the methods of the invention may be used in these situations as well.

It also is possible to take the increased numbers of hematopoietic progenitor cells produced according to the invention and stimulate them with hematopoietic growth agents that promote hematopoietic cell maintenance, expansion and/or differentiation, to yield the more mature blood cells, in vitro. Such expanded populations of blood cells may be applied in vivo as described above, or may be used experimentally as will be recognized by those of ordinary skill in the art. Such differentiated cells include those described above, as well as T cells, plasma cells, erythrocytes, megakaryocytes, basophils, polymorphonuclear leukocytes, monocytes, macrophages, eosinohils and platelets.

In the preferred embodiments of the invention, the hematopoietic progenitor cells are continuously cultured for an extended period of time, and aliquots of the cultured cells are harvested spaced apart in time or intermittently. "Harvesting hematopoietic cells" is defined as the dislodging or separation of cells from the matrix. This can be accomplished using a number of methods, such as enzymatic, centrifugal, electrical or by size, or the one preferred in the present invention, by flushing of the cells using the media in which the cells are incubated. The cells can be further collected and separated. "Harvesting steps spaced apart in time" or "intermittent harvest of cells" is meant to indicate that a portion of the cells are harvested, leaving behind another portion of cells for their continuous culture in the established media, maintaining a continuous source of the original cells and their characteristics. Harvesting "at least a portion of" means harvesting a subpopulation of or the entirety of. Thus, as will be understood by one of ordinary skill in the art, the invention can be used to expand the number of hematopoietic progenitor cells, all the while harvesting portions of those cells being expanded for treatment to develop even larger populations of differentiated cells.

In all of the culturing methods according to the invention, except as otherwise provided, the media used is that which is conventional for culturing cells. Examples include RPMI, DMEM, ISCOVES, etc. Typically these media are supplemented with human or animal plasma or serum. Such plasma or serum can contain small amounts of hematopoietic growth factors. The media used according to the present invention, however, can depart from that used conventionally in the prior art. In particular, it has been discovered, surprisingly, that hematopoietic progenitor cells can be cultured on the matrices described above for extended periods of time without the need for adding any exogenous growth agents (other than those which may be contained in plasma or serum, hereinafter "serum"), without inoculating the environment of the culture with stromal cells and without using stromal cell conditioned media. Prior to the present invention, at least one of the foregoing agents was believed necessary in order to culture hematopoietic progenitor cells.

The growth agents of particular interest in connection with the present invention are hematopoietic growth factors. By hematopoietic growth factors, it is meant factors that influence the survival, proliferation or differentiation of hematopoietic cells. Growth agents that affect only survival and proliferation, but are not believed to promote differentiation, include the interleukins 3, 6 and 11, stem cell ligand and FLT-3 ligand. Hematopoietic growth factors that promote differentiation include the colony stimulating factors such as GMCSF, GCSF, MCSF, Tpo, Epo, Oncostatin M, and interleukins other than IL-3, 6 and 11. The foregoing factors are well known to those of ordinary skill in the art. Most are commercially available. They can be obtained by purification, by recombinant methodologies or can be derived or synthesized synthetically.

In one aspect of the invention, the hematopoietic progenitor cells are cultured in an environment that is free of inoculated stromal cells, stromal cell conditioned medium and exogenously added hematopoietic growth factors that promote differentiation of hematopoietic cells, other than serum. By "inoculated" stromal cells, it is meant that the cell culture chamber is free of stromal cells which have been introduced into the chamber as an inoculum for promoting survival, proliferation or differentiation of the hematopoietic progenitor cells, excluding, however, stromal cells which are contained naturally in the isolate blood product.

"Stromal cells" as used herein comprise fibroblasts and mesenchymal cells, with or without other cells and elements, and can be seeded prior to, or substantially at the same time as, the hematopoietic progenitor cells, therefore establishing conditions that favor the subsequent attachment and growth of hematopoietic progenitor cells. Fibroblasts can be obtained via a biopsy from any tissue or organ, and include fetal fibroblasts. These fibroblasts and mesenchymal cells may be transfected with exogenous DNA that encodes, for example, one of the hematopoietic growth factors described above.

"Stromal cell conditioned medium" refers to medium in which the aforementioned stromal cells have been incubated. The incubation is performed for a period sufficient to allow the stromal cells to secrete factors into the medium. Such "stromal cell conditioned medium" can then be used to supplement the culture of hematopoietic progenitor cells promoting their proliferation and/or differentiation.

Thus, when cells are cultured without any of the foregoing agents, it is meant herein that the cells are cultured without the addition of such agent except as may be present in serum, ordinary nutritive media or within the blood product isolate, unfractionated or fractionated, which contains the hematopoietic progenitor cells.

The culture of the hematopoietic cells preferably occurs under conditions to increase the number of such cells and/or the colony forming potential of such cells. The conditions used refer to a combination of conditions known in the art (e.g., temperature, $CO_2$ and $O_2$ content, nutritive media, etc.). The time sufficient to increase the number of cells is a time that can be easily determined by a person skilled in the art, and can vary depending upon the original number of cells seeded. As an example, discoloration of the media can be used as an indicator of confluency. Additionally, and more precisely, different volumes of the blood product can be cultured under identical conditions, and cells can be harvested and counted over regular time intervals, thus generating the "control curves". These "control curves" can be used to estimate cell numbers in subsequent occasions.

The conditions for determining colony forming potential are similarly determined. Colony forming potential is the ability of a cell to form progeny. Assays for this are well known to those of ordinary skill in the art and include seeding cells into a semi-solid, treating them with growth factors and counting the number of colonies.

According to another aspect of the invention a method for in vivo maintenance, expansion and/or differentiation of hematopoietic progenitor cells is provided. The method involves implanting into a subject a porous solid matrix having pre-seeded hematopoietic progenitor cells and hematopoietic progenitor cell progeny. Implantation of matrices similar to the matrices of the invention is well known in the art (Stackpool, G J, et al, Combined Orthopaedic Research Societies Meeting, Nov. 6–8, 1995, San Diego, Calif., Abstract Book p. 45; Turner, T M, et al., 21st Annual Meeting of the Society for Biomaterials, March 18–22, San Francisco, Calif., Abstract Book p. 125). Such matrices are biocompatible (i.e., no immune reactivity-no rejection) and can be implanted and transplanted in a number of different tissues of a subject. Such methods are useful in a variety of ways, including the study of hematopoietic progenitor cell maintenance, expansion and/or differentiation in vivo, in a number of different tissues of a subject, or in different subjects.

As used herein, a subject is a human, non-human primate, cow, horse, pig, sheep, goat, dog, cat or rodent. Human hematopoietic progenitor cells and human subjects are particularly important embodiments. As described above, when the matrices of the invention are used for such in vivo implantation studies, biological agents that promote angiogenesis (vascularization) and/or prevent/reduce inflammation may also be used for coating of the matrices. Preferred biological agents are as described above. Also as described above, the hematopoietic progenitor cells are pre-seeded onto the porous solid matrix and cultured in vitro according to the invention, before implantation into a subject. According to the invention, an amount of the cells is introduced in vitro into the porous solid matrix, and cultured in an environment that is free of inoculated stromal cells, stromal cell conditioned medium, and exogenously added hematopoietic growth factors that promote hematopoietic cell maintenance, expansion and/or differentiation, other than serum. Implantation is then carried out.

The invention also involves the unexpected discovery that hematopoietic progenitor cells can be more efficiently transduced if the transduction occurs while the hematopoietic progenitor cells are on and within a solid porous matrix as described above. As used herein, "transduction of hematopoietic cells" refers to the process of transferring exogenous genetic material into a cell of hematopoietic origin. The terms "transduction", "transfection" and "transformation" are used interchangeably throughout this letter, and refer to the process of transferring exogenous genetic material into a cell. As used herein, "exogenous genetic material" refers to nucleic acids or oligonucleotides, either natural or synthetic, that are introduced into the hematopoietic progenitor cells. The exogenous genetic material may be a copy of that which is naturally present in the cells, or it may not be naturally found in the cells. It typically is at least a portion of a naturally occuring gene which has been placed under operable control of a promoter in a vector construct.

Various techniques may be employed for introducing nucleic acids into cells. Such techniques include transfection of nucleic acid-$CaPO_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid according to the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

In the present invention, the preferred method of introducing exogenous genetic material into hematopoietic cells is by transducing the cells in situ on the matrix using replication deficient retroviruses. Replication-deficient retroviruses are capable of directing synthesis of all virion proteins, but are incapable of making infectious particles. Accordingly, these genetically altered retroviral vectors have general utility for high-efficiency transduction of genes in cultured cells, and specific utility for use in the method of the present invention. Retroviruses have been used extensively for transferring genetic material into cells. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with the viral particles) are provided in the art.

The major advantage of using retroviruses is that the viruses insert efficiently a single copy of the gene encoding the therapeutic agent into the host cell genome, thereby permitting the exogenous genetic material to be passed on to the progeny of the cell when it divides. In addition, gene promoter sequences in the LTR region have been reported to enhance expression of an inserted coding sequence in a variety of cell types. The major disadvantages of using a retrovirus expression vector are (1) insertional mutagenesis, i.e., the insertion of the therapeutic gene into an undesirable position in the target cell genome which, for example, leads to unregulated cell growth and (2) the need for target cell proliferation in order for the therapeutic gene carried by the vector to be integrated into the target genome. Despite these apparent limitations, delivery of a therapeutically effective amount of a therapeutic agent via a retrovirus can be efficacious if the efficiency of transduction is high and/or the number of target cells available for transduction is high.

Yet another viral candidate useful as an expression vector for transformation of hematopoietic cells is the adenovirus, a double-stranded DNA virus. Like the retrovirus, the adenovirus genome is adaptable for use as an expression vector for gene transduction, i.e., by removing the genetic information that controls production of the virus itself. Because the adenovirus functions usually in an extrachromosomal fashion, the recombinant adenovirus does not have the theoretical problem of insertional mutagenesis. On the other hand, adenoviral transformation of a target hematopoietic cell may not result in stable transduction. However, more recently it has been reported that certain adenoviral sequences confer intrachromosomal integration specificity to carrier sequences, and thus result in a stable transduction of the exogenous genetic material.

Thus, as will be apparent to one of ordinary skill in the art, a variety of suitable vectors are available for transferring exogenous genetic material into hematopoietic cells. The selection of an appropriate vector to deliver a therapeutic agent for a particular condition amenable to gene replacement therapy and the optimization of the conditions for insertion of the selected expression vector into the cell, are within the scope of one of ordinary skill in the art without the need for undue experimentation. The promoter characteristically has a specific nucleotide sequence necessary to initiate transcription. Optionally, the exogenous genetic material further includes additional sequences (i.e., enhancers) required to obtain the desired gene transcription activity.

For the purpose of this discussion an "enhancer" is simply any nontranslated DNA sequence which works contiguous with the coding sequence (in cis) to change the basal transcription level dictated by the promoter. Preferably, the exogenous genetic material is introduced into the hematopoietic cell genome immediately downstream from the promoter so that the promoter and coding sequence are operatively linked so as to permit transcription of the coding sequence. A preferred retroviral expression vector includes an exogenous promoter element to control transcription of the inserted exogenous gene. Such exogenous promoters include both constitutive and inducible promoters.

Naturally-occurring constitutive promoters control the expression of essential cell functions. As a result, a gene under the control of a constitutive promoter is expressed under all conditions of cell growth. Exemplary constitutive promoters include the promoters for the following genes which encode certain constitutive or "housekeeping" functions: hypoxanthine phosphoribosyl transferase (HPRT), dihydrofolate reductase (DHFR) (Scharfmann et al., Proc. Natl. Acad. Sci. USA 88:4626–4630 (1991)), adenosine deaminase, phosphoglycerol kinase (PGK), pyruvate kinase, phosphoglycerol mutase, the actin promoter (Lai et al., Proc. Natl. Acad. Sci. USA 86: 10006–10010 (1989)), and other constitutive promoters known to those of skill in the art. In addition, many viral promoters function constitutively in eucaryotic cells. These include: the early and late promoters of SV40; the long terminal repeats (LTRS) of Moloney Leukemia Virus and other retroviruses; and the thymidine kinase promoter of Herpes Simplex Virus, among many others. Accordingly, any of the above-referenced constitutive promoters can be used to control transcription of a heterologous gene insert.

Genes that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic agent in the genetically modified hematopoietic cell. Selection and optimization of these factors for delivery of a therapeutically effective dose of a particular therapeutic agent is deemed to be within the scope of one of ordinary skill in the art without undue experimentation, taking into account the above-disclosed factors and the clinical profile of the patient.

In addition to at least one promoter and at least one heterologous nucleic acid encoding the therapeutic agent, the expression vector preferably includes a selection gene, for example, a neomycin resistance gene, for facilitating selection of hematopoietic cells that have been transfected or transduced with the expression vector. Alternatively, the hematopoietic cells are transfected with two or more expression vectors, at least one vector containing the gene(s) encoding the therapeutic agent(s), the other vector containing a selection gene. The selection of a suitable promoter, enhancer, selection gene and/or signal sequence (described below) is deemed to be within the scope of one of ordinary skill in the art without undue experimentation.

The selection and optimization of a particular expression vector for expressing a specific gene product in an isolated hematopoietic cell is accomplished by obtaining the gene, preferably with one or more appropriate control regions (e.g., promoter, insertion sequence); preparing a vector construct comprising the vector into which is inserted the gene; transfecting or transducing cultured hematopoietic cells in vitro with the vector construct; and determining whether the gene product is present in the cultured cells.

genes encoding viral antigens, tumor antigens, cytokines (e.g. tumor necrosis factor) and inducers of cytokines (e.g. endotoxin).

The invention also provides various apparatus for carrying out the methods of the invention. The preferred apparatus is depicted in FIG. 1. The principle components of the embodiment depicted in FIG. 1 are a pair of cell culture chambers, one for continuously culturing hematopoietic progenitor cells in an environment which promotes the

TABLE 1

Human Gene Therapy Protocols Approved by RAC: 1990–1994

| | | |
|---|---|---|
| Severe combined immune deficiency (SCID) due to ADA deficiency | Autologous lymphocytes transduced with human ADA gene | Jul. 31, 1990 |
| Advanced cancer | Tumor-infiltrating lymphocytes transduced with tumor necrosis factor gene | Jul. 31, 1990 |
| Advanced cancer | Immunization with autologous cancer cells transduced with tumor necrosis factor gene | Oct. 07, 1991 |
| Advanced cancer | Immunization with autologous cancer cells transduced with interleukin-2 gene | Oct. 07, 1991 |
| Asymptomatic patients infected with HIV-1 | Murine Retro viral vector encoding HIV-1 genes [HIV-IT(V)] | Jun. 07, 1993 |
| AIDS | Effects of a transdominant form of rev gene on AIDS intervention | Jun. 07, 1993 |
| Advanced cancer | Human multiple-drug resistance (MDR) gene transfer | Jun. 08, 1993 |
| HIV infection | Autologous lymphocytes transduced with catalytic ribozyme that cleaves HIV-1 RNA (Phase I study) | Sep. 10, 1993 |
| Metastatic melanoma | Genetically engineered autologous tumor vaccines producing interleukin-2 | Sep. 10, 1993 |
| HIV infection | Murine Retro viral vector encoding HIV-IT(V) genes (open label Phase I/II trial) | Dec. 03, 1993 |
| HIV infection (identical twins) | Adoptive transfer of syngeneic cytotoxic T lymphocytes (Phase I/II pilot study) | Mar. 03, 1994 |
| Breast cancer (chemo-protection during therapy) | Use of modified Retro virus to introduce chemotherapy resistance sequences into normal hematopoietic cells (pilot study) | Jun. 09, 1994 |
| Fanconi's anemia | Retro viral mediated gene transfer of the Fanconi anemia complementation group C gene to hematopoietic progenitors | Jun. 09, 1994 |
| Metastatic prostate carcinoma | Autologous human granulocyte macrophage-colony stimulating factor gene transduced prostate cancer vaccine *(first protocol to be approved under the accelerated review process; ORDA = Office of Recombinate DNA Activities) | ORDA/NIH Aug. 03, 1994* |
| Metastatic breast cancer | In vivo infection with breast-targeted Retro viral vector expressing antisense c-fox or antisense c-myc RNA | Sep. 12, 1994 |
| Metastatic breast cancer (refractory or recurrent) | Non-viral system (liposome-based) for delivering human interleukin-2 gene into autologous tumor cells (pilot study) | Sep. 12, 1994 |
| Mild Hunter syndrome | Retro viral-mediated transfer of the iduronate-2-sulfatase gene into lymphocytes | Sep. 13, 1994 |
| Advanced mesothelioma | Use of recombinant adenovirus (Phase I study) | Sep. 13, 1994 |

The foregoing (Table 1), represent only examples of genes that can be delivered according to the methods of the invention. Suitable promoters, enhancers, vectors, etc., for such genes are published in the literature associated with the foregoing trials. In general, useful genes replace or supplement function, including genes encoding missing enzymes such as adenosine deaminase (ADA) which has been used in clinical trials to treat ADA deficiency and cofactors such as insulin and coagulation factor VIII. Genes which affect regulation can also be administered, alone or in combination with a gene supplementing or replacing a specific function. For example, a gene encoding a protein which suppresses expression of a particular protein-encoding gene can be administered. The invention is particularly useful in delivering genes which stimulate the immune response, including survival and proliferation of the progenitor cells, but not the differentiation of the progenitor cells. The other cell culture chamber (which can be one or more second cell culture chambers) is for receiving intermittently portions of the cells cultured in the first cell culture chamber for culturing in an environment that includes growth factors that promote differentiation of hematopoietic progenitor cells.

Referring to FIG. 1, a first cell culture chamber 10, and a second cell culture chamber 12 are shown. The cell culture chambers 10, 12 have walls defining the inside of the chamber. A connection conduit 16 provides fluid communication between the first and second cell culture chambers. The connection conduit can be any fluid conduit between the first and second cell culture chambers, although in the embodiment depicted, the connection conduit 16 includes a plurality of valves and a collection chamber, described in greater detail below. Each of the first and second cell culture chambers 10, 12 contain a porous solid matrix 18, as described in detail above. The porous solid matrix 18 is supported by matrix supports 20 which hold the matrix 18 away from the walls 14 to provide a space 22 permitting circulation of media throughout the matrix 18. Preferably there is a seal which restricts fluid flow around the matrix, forcing the fluid to flow through the matrix.

The first cell culture chamber 10 is provided with an inlet port 24 which communicates with a media input conduit 26 for supplying media to the first culture chamber. The port 24 or the media input conduit 26 can be provided with a valve (not shown) for controlling the flow of media into the first cell culture chamber 10.

The first cell culture chamber has a top 28 which closes the first cell culture chamber. This top 28 may engage the walls 14 of the first cell culture chamber in a sealing fashion or, alternatively, can engage the walls 14 of the first cell culture chamber in a manner to permit the exchange of gases as is conventional in certain cell culture apparatus. In the embodiment depicted, the top sealingly engages the walls. A sample port 30 is provided in the top 28 and communicates with a sampling conduit 32 for permitting materials to be added into or removed from the first cell culture chamber. Preferably, as shown in connection with the second cell culture chamber and described in more detail below, a second conduit can be provided (an augmentation conduit), whereby the sample conduit is for removing material from the cell culture chamber whereas the augmentation conduit is for introducing material into the cell culture chamber. The sample port 30 and/or sample conduit 32 can be provided with a valve (not shown) for isolating the internal environment of the first cell culture chamber from external environmental influences.

The first cell culture chamber 10 also has an outlet port 34 communicating with the connection conduit 16.

Turning to the second cell culture chamber 12, wherein like numerals indicate like parts, the second cell culture chamber has walls 14 for containing a porous solid matrix 18 supported by matrix supports 20. The top 28 of the second cell culture chamber 12 is sealingly engaged with the walls 14 of the second cell culture chamber. The top includes a sample port 30 and a sample conduit 32 communicating with the sample port 30 for obtaining samples of material from inside of the second cell culture chamber. The top 28 of the second cell culture chamber 12 also includes an outlet port 34 communicating with an outlet conduit 36 whereby, preferably, media may be circulated continuously throughout the system being introduced via the media input conduit 26 and leaving the system via the media outlet conduit 36. The second cell culture chamber 12 also includes an augmentation conduit 38 for supplying the second cell culture chamber with materials, preferably hematopoietic growth factors that induce differentiation, to the second cell culture chamber.

Turning to the connection conduit 16, as mentioned above this can be any conduit, and preferably there is at least one valve between the first cell culture chamber 10 and the second cell culture chamber 12 along this conduit, whereby the flow of media between the first and second cell culture chambers can be interrupted. In the embodiment depicted, the connection conduit 16 includes a first portion 40 exiting the first cell-culture chamber 10 and terminating in fluid communication with a collection chamber 42. A second portion 44 of the connection conduit provides fluid communication from the collection chamber 42 to the second cell culture chamber 12. The first portion 40 is interrupted by a first portion valve 46 and the second portion 44 of the connection conduit 16 is interrupted by a second portion valve 48.

The collection chamber also is in fluid communication with a flushing conduit 50 which has a flushing conduit valve 52.

In one embodiment of operating the apparatus of the invention, the valve (not shown) at inlet port 24 and outlet port 34, first portion valve 46, second portion valve 48, and outlet conduit valve (not shown) at the outlet port 34 of second cell culture chamber are open. Valves (not shown) of the sample ports 30 of the first and second cell culture chambers 10, 12, valve (not shown) at the port of the second cell culture chamber 12 communicating with the augmentation conduit 38 is closed and the flushing conduit valve 52 is closed. In this manner, media can be perfused through the first cell culture chamber, through the connection conduit and through the second cell culture chamber continuously, if desired. As will be readily understood, media introduced into the first cell culture chamber can be prevented from contacting the second cell culture chamber by closing valve 48 and opening valve 52. Likewise, the second cell culture chamber can receive media different from that received by the first cell culture chamber by opening the valve at the port communicating with the second cell culture chamber via the augmentation conduit 38, which may provide the only media to the second cell culture chamber, may augment media received into the second cell culture chamber from the first cell culture chamber or may augment media received via flushing conduit 50. In addition to providing for the differential media requirement as describe above for the first culturing step and the second culturing steps of the invention, the present apparatus also provides for the transfer of cells between the chambers via the conduit arrangement shown. In this embodiment, a gentle pulse of fluid is applied to the first cell culture chamber, sufficient to dislodge hematopoietic progenitor cells from the porous solid matrix in the first culture chamber. These cells then can be carried by fluid movement from the first cell culture chamber into the collection chamber. The collection chamber can, if desired, be provided with a means for temporarily maintaining the cells in the chamber such as by a moveable membrane, filter or the like, although such structure is not necessary for the operation of the apparatus of the invention. Once the cells are within the collection chamber 42, valve 46 can be closed. Subsequently, valve 52 can be opened, and the cells can be flushed by fluid pressure from the collection chamber 42 into the second cell culture chamber 12. In this manner, as a result of closing valve 46, it is ensured that hematopoietic growth factors that have been introduced into the second cell culture chamber do not flow backwards into the first cell culture chamber, contaminating the first cell culture chamber with unwanted material. The mere pressure due to continuous flow of media, however, may be sufficient to prevent backflow and the closing of valve 46 may be unnecessary. Numerous modifications to the apparatus shown will be apparent to those of ordinary skill in the art. The important aspects of the apparatus are the provision of two cell culture chambers and the mechanism for fluid communication between them, with a valve arrangement, etc. whereby the first cell culture chamber cannot be contaminated with unwanted materials which are added downstream into the second cell culture chamber.

EXAMPLES

Experimental Procedures

Long-Term Cultures:

$CD34^+$ hematopoietic progenitor cells were derived from human bone marrow (Poietic Technologies) isolated using magnetic anti-human $CD34^+$ beads (Dynal, Lake Success, N.Y.) and separated from these beads using an anti-idiotype antibody (Detachabead, Dynal). All culture conditions were seeded with $2\times10^5$ cells to ensure enough cells for all analyses, particularly from control cultures. While preliminary data indicated that $CD34^+$ cells would survive well in Cellfoam, it was anticipated that culture in the absence of cytokines would lead to reduced cell numbers in control cultures. For the purposes of planning the experiments, we estimated that up to 75% of the cells (or $1.5\times10^5$ cells) may be lost, leaving $5\times10^4$ cells per reactor, enough cells to perform flow cytometry, multipotency colony assays and LTCIC (Long Term Culture Initiating Cell) analyses. Cultures were performed in duplicate to provide side by side comparisons of each culture time point. Thus, each culture time point used two reactors, each seeded with $2\times10^5$ $CD34^+$ cells.

$2\times10^5$ $CD34^+$ cells in 1 ml of medium were seeded onto plastic dishes coated with bone marrow stromal cells (plastic/BMS), plastic coated with fibronectin (plastic/FN), or into Cellfoam. Primate bone marrow stromal cells grown for 2–3 weeks to isolate the heterogeneous adherent, fibroblast-like population of cells capable of supporting HSCs in short-term assays.

All cultures contained 1 ml of Myelocult medium (Stem Cell Technologies, Vancouver, Canada), a medium for long-term HPC culture. No exogenous cytokines were added to this medium. After 1, 1.5, 3 and 6 week of culture as above with weekly medium changes, all cells (adherent and non-adherent) were harvested from all culture conditions/reactors, counted, and surface antigen stained. We recovered adherent cells because some primitive HPCs or HPC subclasses may exhibit adherent properties which would prevent their being harvested by simple washing or centrifugation. Non-adherent cells were harvested from Cellfoam by simple centrifugation for 10 minutes at 1500 rpm (approximately 250×G) in a table top centrifuge. Adherent cells were harvested with a non-trypsin isolation solution (Cell Dissociation Solution, Sigma, St. Louis, Mo.) to minimize alteration of surface staining characteristics. To recover adherent cells from Cellfoam, units were washed twice by immersion into PBS, saturated by brief vortexing in an excess of Cell Dissociation Solution, incubated for 20 minutes at 37° C., and centrifuged at 1500 rpm for 10 minutes. Non-adherent cells were recovered from plastic/stroma and plastic/FN systems by gentle washing; adherent cells were isolated using the Cell Dissociation Solution as described above. Antibodies used for surface phenotype determination will include anti-CD34 (Qbend10, Immunotech), anti-CD38 (OKT10, ATCC, Bethesda, Md.) and anti-CD45 (Becton Dickinson) antibodies to evaluate progenitor cell distributions. Flow cytometry analysis of the cells was performed using multi-parameter FACScan flow cytometry analysis. Appropriate controls included matched isotype antibodies to establish positive and negative quadrants, as well as appropriate single color stains to establish compensation. For each sample, at least 10,000 list mode events were collected.

Colony-formation Assays:

To determine whether HPCs cultured in Cellfoam for up to six weeks retain the ability to produce myeloid and erythroid colonies, we performed traditional methylcellulose assays. Equal numbers of cells which have been isolated from Cellfoam, plastic/BMS or plastic/FN cultures, as described above, were added at $1\times10^4$/ml to 3.0 ml of methylcellulose medium with cytokines (IL-3 20 ng/ml; GMCSF 30 ng/ml; erythropoietin 3 IU/ml; stem cell factor 50 ng/ml; all Stem Cell Technologies, Vancouver) plus 0.5 ml of DMEM (2% FCS, 10 IU/ml penicillin, 10 µg/ml streptomycin, 1 mM L-glutamine). 1.5 ml of this mixture was added to a scored petri dish using a syringe and a blunt needle to avoid bubbles. Duplicate assays were performed for each condition. The two duplicate petri dishes were then placed in an incubator with 5% $CO_2$ at 37° C. for 10–21 days. After 10–21 days, the number of colonies were determined by manual counting. Positive colonies were scored on the basis of an accumulation of 20 or more cells. Erythroid colonies were scored after 14–21 days on the basis of a gold-brown pigment, demonstrating hemoglobin, whereas myeloid colonies were identified by their predominantly transparent appearance. Counts were done in duplicate.

T-Cell Lymphopoiesis:

The ability of cultured HPCs to foster T-cell lymphopoiesis was assessed in an in vitro T-cell differentiation assay in which cells isolated from Cellfoam or other cultures are seeded onto thymic stroma tissue and evaluated for the ability to produce mature T cells as assessed by CD4 and CD8 single positivity and CD4CD8 double positivity antibody staining. The T-cell differentiation assay utilizes a bed of primate thymic stromal cells plated into 24 well plates to support the differentiation of hematopoietic progenitor cells into thymocytes and T cells (see U.S. Pat. No. 5,677,139, incorporated in its entirety herein by reference). In this assay, thymic monolayer cultures are prepared from third trimester or neonatal rhesus thymic tissue by mincing tissue and then digesting into a single cell suspension using collagenase and DNAase. Thymic stroma cell suspensions, which can be used either fresh or from cryopreserved samples, are then plated into 24 well plates. After two days, the non-adherent cells are removed and the adherent cell layer washed vigorously to remove any loose cells. After 6 days in culture, the isolated culture cells are added to the monolayer. After 10–14 days, the cultures are evaluated for the presence of immature double positive lymphocytes ($CD3^+CD4^+CD8^+$), and mature single positive lymphocytes ($CD3^+CD4^+CD8^-$ and $CD3^+CD4^-CD8^+$).

In parallel for all experiments, dual controls consisting of unfractionated bone marrow and $CD34^+$ cells, neither of which had been cultured in Cellfoam, were evaluated for colony-forming potential and T lymphopoiesis in the assays described above. The overall number of colonies indicates the relative number of stem cells present in Cellfoam, plastic or bone marrow stroma cultures that retained the ability to produce differentiated erythroid or myeloid colonies in the presence of cytokines.

LTCIC Assays and LTCIC Transduction:

As an indicator of the ability of Cellfoam to support cells which have long-term repopulating potential, modified LTCIC assays were performed. LTCICs are relatively quiescent cells that exhibit the characteristic of prolonged survival in bone marrow stroma cultures, and it is during this time that they gradually acquire the phenotype required to give rise to erythroid and myeloid colonies in vitro. An important goal of the proposed research is to determine the utility of Cellfoam in supporting the retroviral transduction of LTCICs in vitro. These cells are relatively quiescent, and thus have been difficult to transduce efficiently. Enhanced transduction may be facilitated by performing biweekly transductions of the cells in Cellfoam over extended periods. Cellfoam cultures were as described above and inoculated with $2 \times 10^5$ cells, and half-volume medium exchange were performed twice a week with high titer retroviral supernatant (PG13LN, from ATCC, grown in an ACS cartridge, titer of $1 \times 10^6$ CFU/ml). The PG13LN vector is prepared as follows: the retroviral producer cell line is inoculated into a cartridge with up to 1800 cm$^2$ of surface and which is separated from circulating tissue culture medium by a semi-permeable membrane with a molecular weight threshold of 10,000 kd. Continuous circulation of medium through the extracapillary space by a peristaltic pump optimizes gas and nutrient exchange resulting in significant increases in retroviral vector production. Average increases in end-point dilution titer of retroviral vector supernatants produced using the bioreactor versus tissue culture flasks are 10–20 fold, with 100 fold increases noted in some instances. The infectious titer of the retroviral supernatants produced in the continuous perfusion cartridges is determined via plaque forming assays on COS cells.

In addition to retroviral medium exchanges, an additional medium exchange with LTCIC medium was performed once a week. Traditional LTCIC cultures utilizing prepared bone marrow stroma acted as controls and were cultured and transduced for the same period of time as parallel Cellfoam cultures. We also attempted to culture LTCICs in plastic wells coated with fibronectin. All culture volumes were identical. Following transduction in each device, methylcellulose CFU assays were performed. Total cells having undergone transduction in each device were resuspended in 3 ml of methylcellulose medium with the addition of the cytokines IL-3 (20 ng/ml), stem cell factor (50 ng/ml), erythropoietin (3 IU/ml) and GMCSF (30 ng/ml), all part of the methylcellulose assay, and re-plated in 35-mm dishes in the presence or absence of the neomycin analog 418 (400–800 μg/ml). After two weeks, colonies were scored using the criteria described above. The colony counts indicate the survival of LTCICs after the initial six-week culture period. The relative survival with G418 versus without G418 indicates the survival of LTCICs that had been transduced during the initial culture periods. The presence of these cells serves as a measure of the survival of long-term repopulating cells, LTCICs, and their relative level of transduction in Cellfoam versus plastic/BMS and plastic/FN. It is important to note that the initial culture of cells in Cellfoam for 6 weeks defines the traditional threshold at which LTCICs are measured. Thus, culturing for 3 or 6 weeks in Cellfoam, followed by 6 weeks in bone marrow stroma LTCIC assays extends the classic definition of LTCICs.

Example 1

Figure 3:
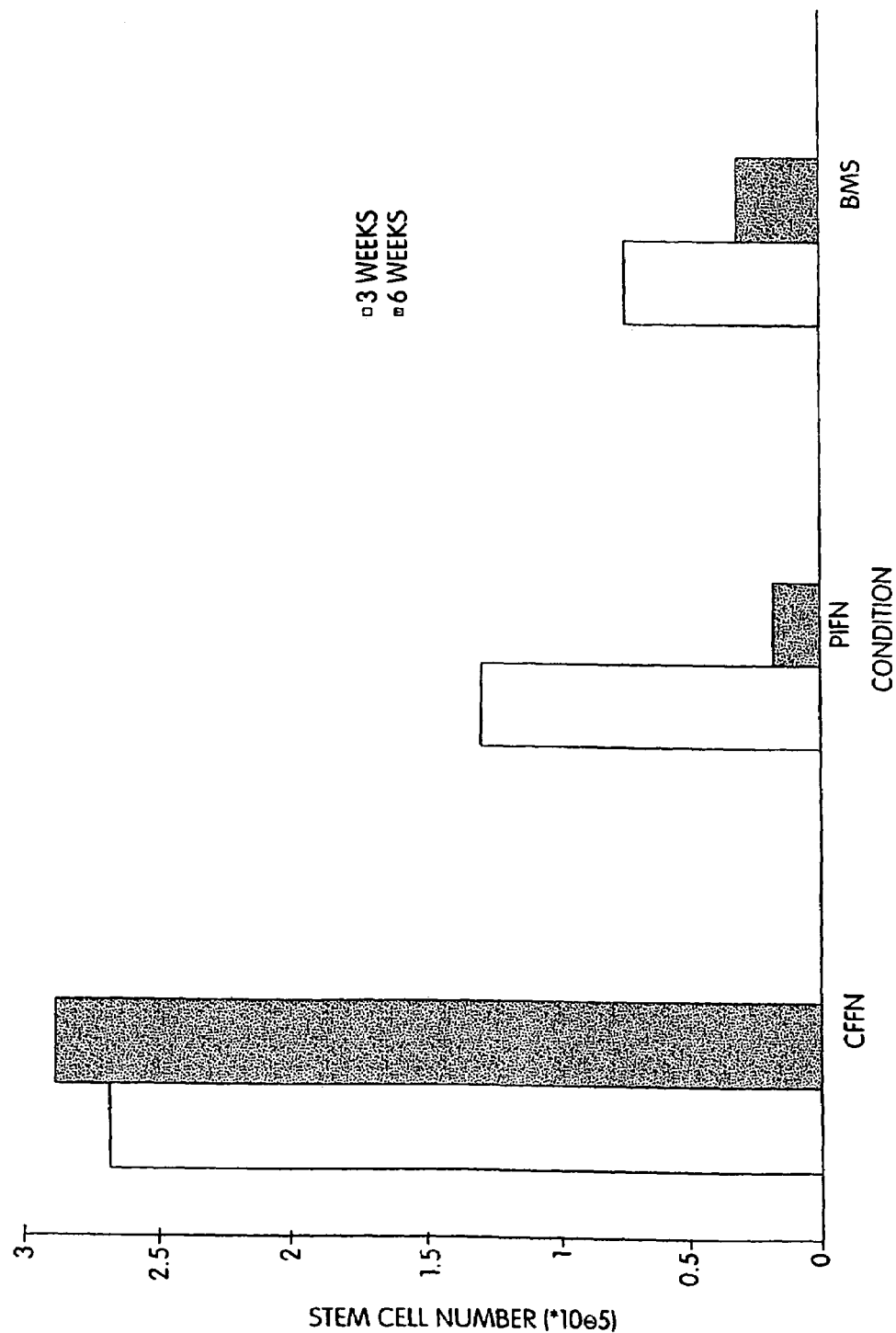
FIG. 3. Survival and expansion of $CD34^+$ HPCs in Cellfoam v. control systems at 3 and 6 weeks.

We performed extended-culture survival studies examining CD34+ HPC cell numbers at 1, 3, and 6 weeks in the absence of supplemented cytokines. Cultures were carried out in fibronectin coated Cellfoam units and compared with bone marrow stroma and fibronectin coated plastic dishes CD34+ HPCs cultured in Cellfoam without cytokine supplementation exhibited enhanced survival and marked enrichment compared to parallel control cultures. The loss of HPCs in control systems supports documentation of their inability to support HPCs without exogenous cytokines. Plastic dish cultures performed similar to BMS. Conversely, at 1 week CD34+ cell counts in Cellfoam were 2.5–3 fold higher than other systems analyzed and had increased 80–110% over input numbers. By 3 and 6 weeks, as many as 6 to 10 times CD34+ cells were detected in Cellfoam versus controls. This increase in cell number was reproducible and in the absence of cytokines. In addition, we were able to count an immature population of cells (phenotype CD34+CD38−) which was enriched in Cellfoam compared to bone marrow stroma cultures at 3 and 6 weeks; results are shown in FIG. 3 (3 weeks—1st column, 6 weeks—2nd column).

Example 2

Figure 4:
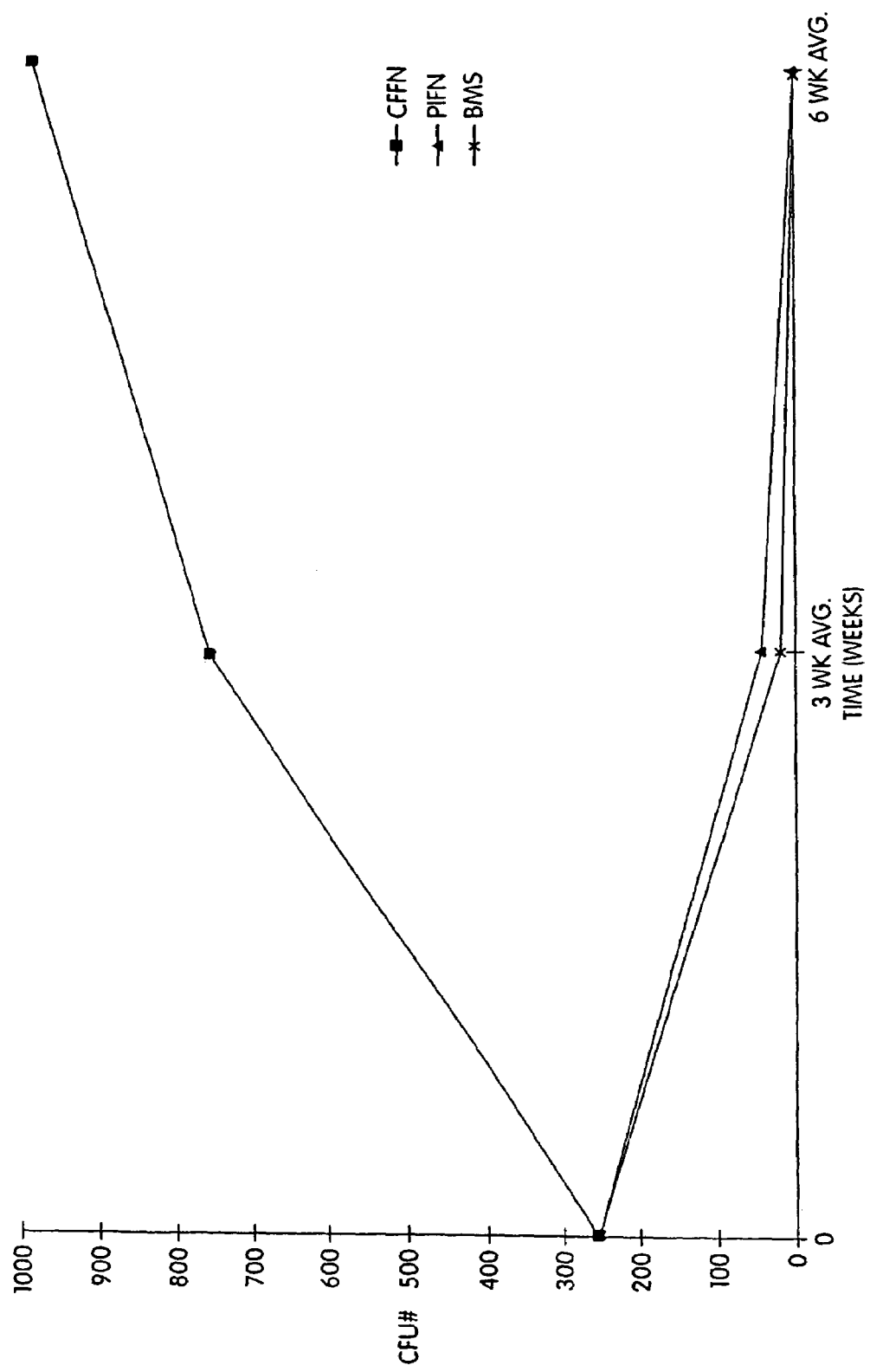
FIG. 4. CFU ability of HSCs isolated from Cellfoam and control cultures.

In addition, we evaluated the multipotency of the population of cells isolated from multi-week cytokine cultures. The assays used were conventional methylcellulose colony-formation assays to evaluate myeloid and erythroid colony-forming cells and a published lymphopoiesis assay to evaluate T cell precursor activity. We observed that HPCs isolated from Cellfoam cultures retain red blood cell (RBC) and white blood cell (WBC) colony forming ability to a greater extent than parallel control cultures. In all cultures the CFU-GM and BFU-E were evaluated; the myeloid:erythroid ratio was approximately 2:1. At 3 weeks, Cellfoam cultures yielded up to 31 times as many colonies compared to controls, an increase of 16 fold over input capabilities (see FIG. 4). By 6 weeks, HPCs had lost essentially all of their colony-forming ability in BMS and plastic-fibronectin cultures. HPCs from Cellfoam is displayed a 1000 fold greater capacity to produce colonies over control-isolated cells (see FIG. 4).

Example 3

The ability of cultured HPCs to foster T-cell lymphopoiesis was assessed in an in vitro T-cell differentiation assay. After termination of Cellfoam and control cultures at 3 and 6 weeks, an aliquot of the combined adherent/non-adherent factions were co-cultured with primary fetal thymic stroma. We evaluated the ability to produce mature T cells as assessed by CD4 and CD8 single positivity and CD4CD8 double positivity antibody staining. When cells were harvested at 3 and 6 weeks from Cellfoam and control cultures and placed in the T-cell assay, only cells recovered from Cellfoam generated T-cell progeny at both time points. Cells recovered from FN/plastic failed to generate T-cell progeny. Cells from BMS cultures generated T-cell progeny at 3 weeks but not at 6 weeks. Progeny derived from Cellfoam included CD4+CD8+ thymocytes, as well as CD4+ and CD8+ cells. Progeny derived from Cellfoam cultures included CD4+CD8+thymocytes as well as CD4$^+$ and CD8$^+$ single positive cells while most of these thymocytes express CD3, an additional indicator of efficient T-cell development. To date, no in vitro culture system has been shown to efficiently and reproducibly support the maintenance of an HPC population that includes T-cell progenitors. As the assessment of multipotency is generally limited to the generation of myeloid and erythroid colonies, the evaluation of T-cell progeny greatly enhances our estimation of the true nature of cells cultured long-term in Cellfoam. As the data demonstrate, Cellfoam was able to support T-cell progenitor survival to a greater extent than controls. Importantly, Cellfoam provides an effective long-term culture system for the maintenance of multipotent HPCs ex vivo.

Example 4

We also examined the ability of Cellfoam to support the survival of LTCICs, cells which may represent more immature hematopoietic progenitors critical to host reconstitution. These studies utilized LTCICs (longer surviving progenitors from cultures up to 14 weeks) that were subsequently plated onto traditional LTCIC plates consisting of irradiated BMS cells. We found that HPCs isolated from fibronectin coated Cellfoam maintained LTCIC over the initial 3 week culture period (9 weeks total in culture). Cellfoam cultures yielded 17.5 times as many LTCICs as BMS cultures. Cellfoam cultures not coated with fibronectin yielded a 4 fold increase in LTCIC activity versus BMS cultures. These data suggest that Cellfoam maintains LTCIC activity to a greater extent than control systems. This provides additional evidence that Cellfoam is advantageous for the culture of HPCs because long-term surviving cells are believed to be an important indicator of primitive hematopoietic progenitor content. Six weeks cultures were followed by 6 weeks in LTCIC assays and 2 weeks in colony assays, cells from plastic cultures produced no LTCICs). Similarly, BMS cultures had lost all viable ECHCPs. However, Cellfoam cultures yielded encouraging LTCIC numbers yielding, on average, 36 times as many LTCICs as BMS cultures. Cellfoam produced 18+/−8 LTCICs per $10^4$ cells compared to 0.5+/−0.7 LTCICs per $10^4$ cells for BMS cultures (p=0.05, n=6). Fibronectin-coated Cellfoam units improved ECPHC preservation approximately 2 fold over uncoated Cellfoam units. Uncoated units yielded 8+/−11 LTCICs per $10^4$ cells, a 16 fold increase over BMS controls. Compared to the 3 week timepoint, the 6 week timepoint maintained approximately half as many LTCICs in Cellfoam. This suggests that static cultures have a finite ability to maintain long term culture cells or that selection of more immature, long-lived cells is ongoing. It is imperative to note that the maintenance of this number of LTCICs at 11 and 14 weeks represents a significant breakthrough in the culturing of HPCs. It has been reported that there is a correlation between the maintenance of long-lived cells and primitive HPCs which includes a subset of cells which may be important contributors of self-renewal and long-term host reconstitution. As our previous data demonstrate, cells cultured over long periods in Cellfoam also retain multipotency, a further indication that the Cellfoam system may represent an enabling technology for providing the most primitive stem cells required for optimal bone marrow transplantation and repopulation of ablated hosts.

Example 5

Additionally, we have examined the transduction of colony forming HPCs, using a Neomycin resistance gene in a PG13LN retroviral vector over a 3 day period. Transduction of colony-forming progenitors in Cellfoam is at least 40–50% more efficient than BMS or plastic systems). Similarly, the transduction efficiency of LTCICs using Cellfoam is improved by about 40–50%. LTCICs were cultured in Cellfoam or BMS for 6 weeks. Retroviral transduction was performed weekly. After 6 weeks, cells were harvested and plated in methylcellulose with and without G418 to assess transduction efficiency. Cells from BMS were unable to produce colonies in the presence or absence of neomycin analog. Conversely, in Cellfoam, we obtained colonies in both G418+ and G418− assays, indicating that LTCIC activity was preserved in Cellfoam in the presence of the retrovirus and that LTCIC transduction could be performed on these cells in Cellfoam with 50% efficiency.

Example 6

We also examined the effect of low level cytokine supplementation on long-term HPC survival and multipotency by culturing hematopoietic cells (including CD34+ cells and immature CD34+38− cells) on Cellfoam. We observed that supplementation with cytokines at levels far below those used in prior art results in increased hematopoietic cell numbers and colony forming activity and maintainance and expansion of immature progenitors. This is in contrast to what research in the field has shown, namely that high levels of cytokines may alter long-term HPC survival and multipotency. Therefore, the ability to use picogram and nanogram levels of cytokines on HPCs cultured on Cellfoam affords the opportunity, for the first time, to expand HPCs without altering their multipotency/function. As will be evident to those of ordinary skill in the art, the invention enables the use of particular cytokines in the nanogram/ml and picogram/ml concentration range to achieve reproducible, practical gains in HPC number and functionality. This unexpected capability has not been possible with other 2-dimensional and 3-dimensional systems of the prior art. The studies described below utilized the following concentrations of cytokines:

| cytokine level: | nanogram (ng) level | picogram (pg) level |
|---|---|---|
| IL-3 | 10 ng/ml | 100 pg/ml |
| IL-6 | 10 ng/ml | 100 pg/ml |
| FLK2 | 25 ng/ml | 250 pg/ml |
| SCF | 25 ng/ml | 250 pg/ml |

Note:
Combination cytokines used constituent cytokines each at the concentration shown.

In the experiments described here, an average of 45,000 CD45+ HPCs cells were inoculated into the culture systems, cultured for one, three or six weeks in Cellfoam or in bone marrow stroma (BMS) or plastic well control systems in the presence of the indicated cytokines and then evaluated for cell numbers and multipotency in colony formation assays. All cultures were performed at least in quadruplicate. Particular emphasis was placed on the yield of CD45+, CD45+ 34+ and CD45+34+38− cells; total cell number was viewed as less meaningful since BMS cultures were pre-seeded with a high number of stromal cells which obfuscated total cell number analysis. Cells were harvested, combining non-adherent and adherent fractions from single wells, and stained with fluorochrome-conjugated monoclonal antibodies to CD45 (to gate on CD45+ hematopoietic cells and preclude stromal cells from analyses) and to CD34 and CD38 progenitor surface molecules.

Figure 5:
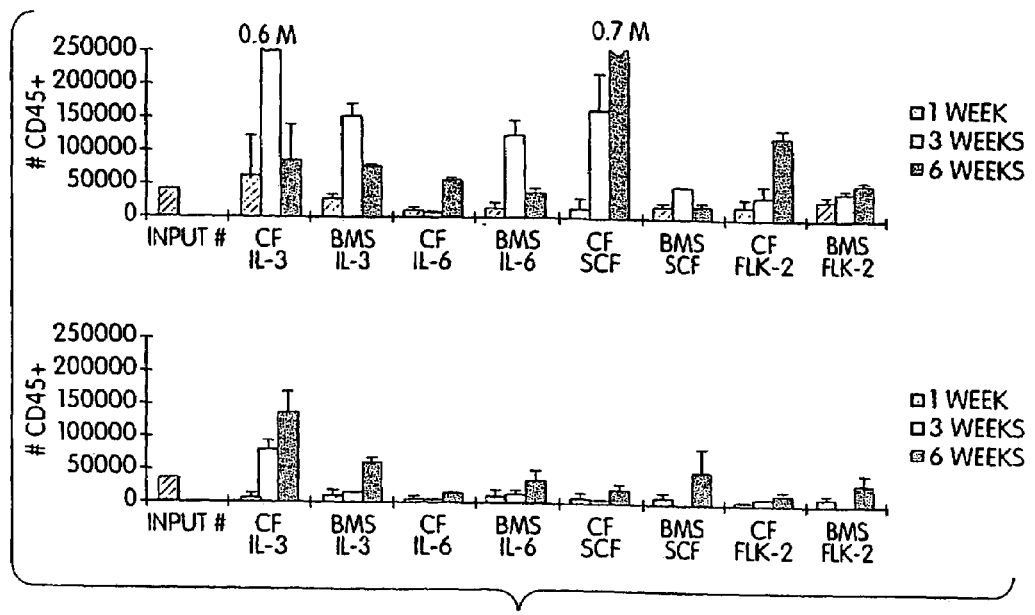
FIG. 5. $CD45^+$ cell number at 1, 3 and 6 weeks in Cellfoam and BMS cultures supplemented with cytokines.
Figure 6:
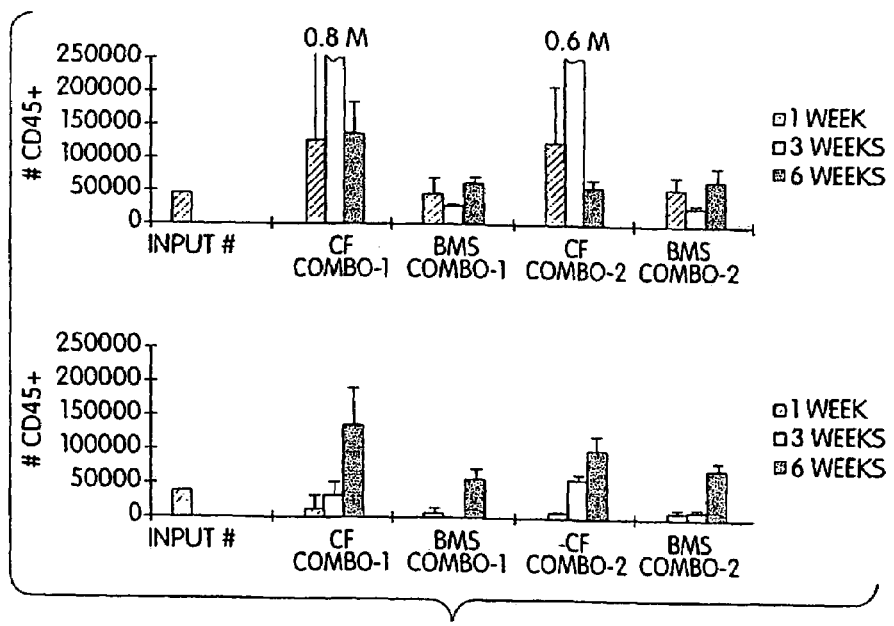
FIG. 6. $CD45^+$ cell number at 1, 3 and 6 weeks in Cellfoam and BMS supplemented with the combination cytokines.

In studies examining the effects of nanogram and picogram concentrations of single cytokines on HPC survival in Cellfoam as compared to bone marrow stroma (BMS), IL-3 and IL-6 showed the greatest cell expansion at three weeks, followed by a decline at six weeks, whereas SCF and FLK2 showed continued expansion from three to six weeks. All four cytokines generated significantly higher cell numbers than input in Cellfoam devices at least at one time point but only IL-3 did so in BMS (FIG. 5, top nanogram, bottom picogram concentrations). Picogram concentrations tended to show consecutive increases in CD45+ cell number from one to three to six weeks (FIG. 5). Combinations consisting of three cytokines each (IL-3+IL-6 and either SCF or FLK) led to increase in cell numbers similar to single cytokines (FIG. 6, top nanogram, bottom picogram concentrations). Similar findings in CD45+ cell counts were obtained for studies comparing Cellfoam and plastic dish cultures.

Figure 7:
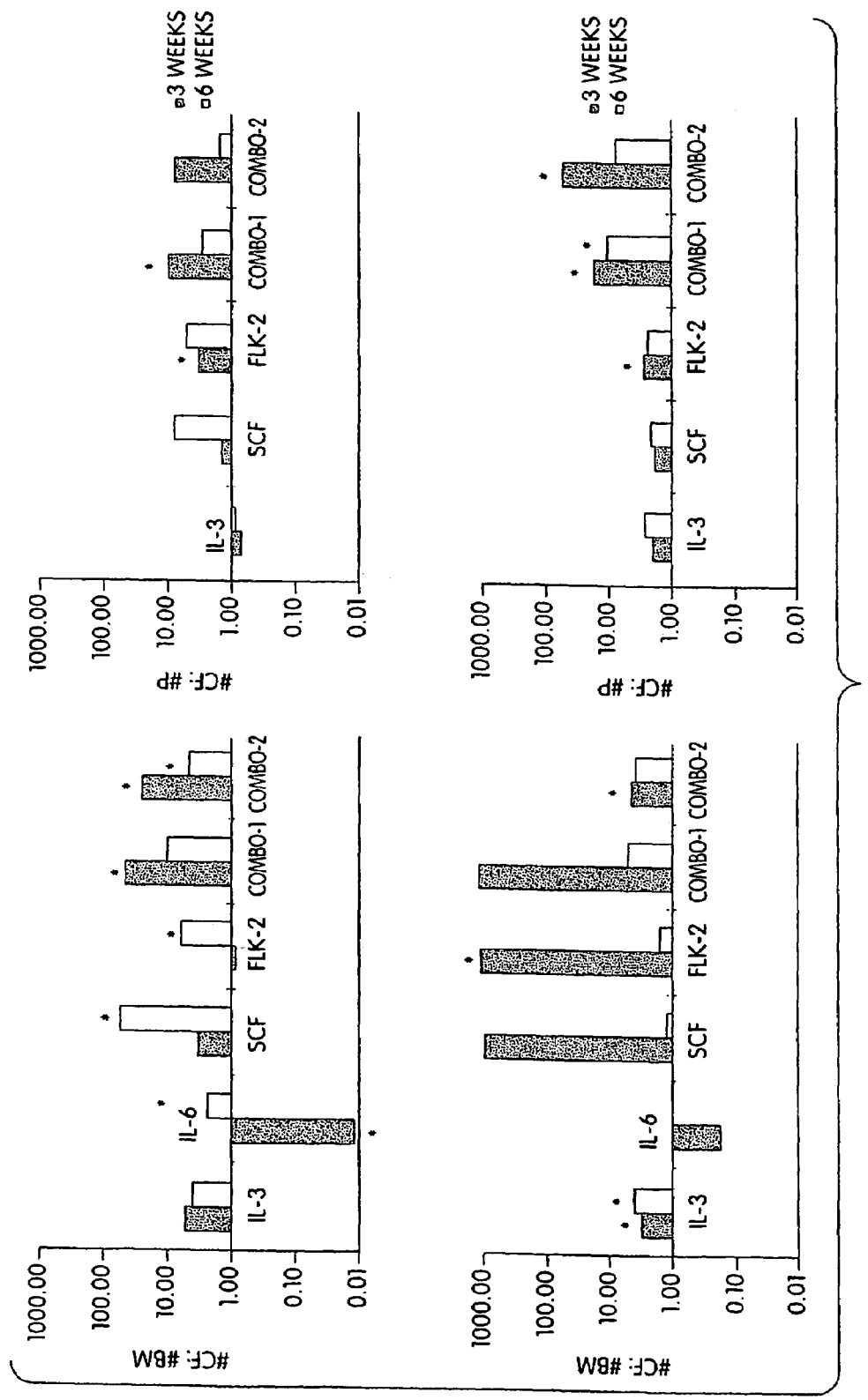
FIG. 7. Fold difference of $CD45^+34^+$ cell yield in Cellfoam cultures as compared to BMS and plastic control cultures at 3 and 6 weeks at nanogram (top) and picogram (bottom) concentrations.

CD45+34+ and CD45+34+38– cell numbers also tended to be higher in Cellfoam than in BMS (FIG. 7, top nanogram, bottom picogram concentrations). Of 32 possible comparisons of cell number v. single cytokine-concentration-time datum points in Cellfoam and BMS cultures at three and six weeks, higher numbers of CD45+34+ and CD45+34+38– cells were observed in Cellfoam in 25 (78%). Of 16 possible comparisons of cell number v. combination cytokine-concentration-time datum points in Cellfoam and BMS at three and six weeks, higher CD45+34+ and CD45+34+38– numbers were observed in Cellfoam in all 16 (100%) (see FIG. 7 for representative CD45+34+ patterns). Statistically significant values are noted with an asterisk in FIG. 7 which compares the fold difference in cell number between Cellfoam and BMS (and plastic; see below). Bars above the 1.00 line indicate the fold higher numbers obtained in Cellfoam as compared to controls; bars below the 1.00 line indicate the fold higher numbers obtained in controls as compared to Cellfoam. Scale is shown on log base for convenience. Asterisks denote statistically significant values. Patterns of fold difference for CD45+34+38– cells were similar to those shown here for CD45+34+ cells.

Similar results to the above were obtained in comparisons of Cellfoam and plastic cultures. Of 24 possible comparisons of cell number v. cytokine-concentration-time datum points at three and six weeks, higher numbers of CD45+34+ and CD45+34+38– cells were observed in Cellfoam in 21 (88%). Of 16 possible datum points for combination cytokine cultures, Cellfoam yielded more cells than plastic in 15 (94%; FIG. 7). Thus, overall, of 88 possible datum points, Cellfoam cultures yielded higher numbers in 77 (88%).

In summary, these data support the conclusion that concentrations of cytokines in concentrations far lower than can be used in conventional systems and which have been used routinely by previous investigators can be effectively used in Cellfoam to increase HPC number. In general, concentration of cytokines between 0.1–0.5 ng/ml promote maintainance of HPCs, while cytokine concentrations higher than about 0.5 ng/ml promote differentiation of HPCs.

Figure 8:
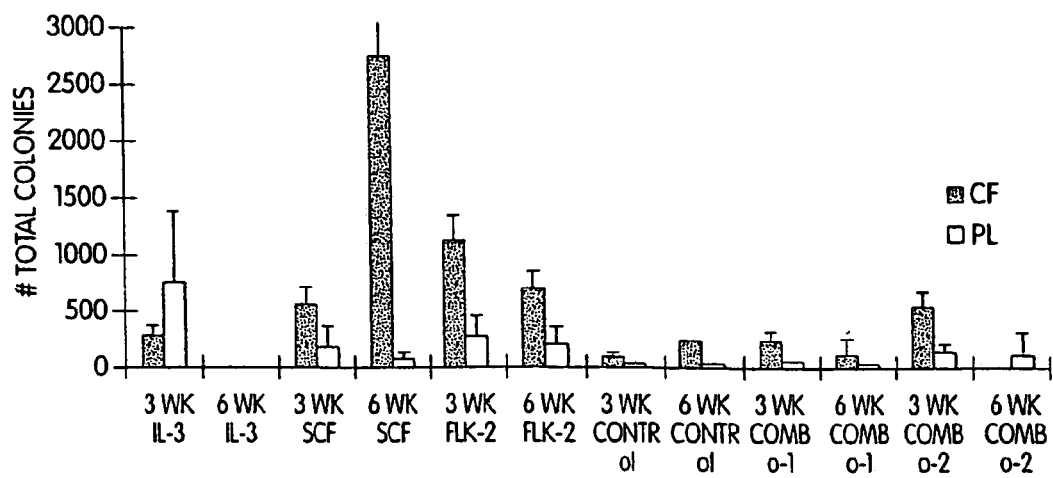
FIG. 8. Total colony activity of cells isolated from Cellfoam and plastic cultures supplemented with cytokines.

The function of cells cultured under these conditions was measured by evaluating in vitro colony forming capabilities utilizing methylcellulose CFU assays. In comparing Cellfoam to plastic cultures, with the exception of IL-3 supplementation colony activity was uniformly greater in Cellfoam than in plastic, ranging from approximately 3 to 36 times greater (FIG. 8). Total CFU activity was derived by multiplying the colony count per 10,000 input cells by the factor for total progenitor number obtained in the three and six week cultures. Control cultures added no cytokines. Thus, Cellfoam yielded both higher cell numbers and higher colony activity than plastic cultures. It is also interesting to note that nanogram concentration cytokine supplementation led to decreases in total colony activity from three to six weeks (with the exception of SCF in Cellfoam cultures) suggesting a time-dependent exposure effect of cytokine augmentation on HPC function. In picogram concentration supplementation experiments using combination cytokines, the drop-off in CFU activity was much less dramatic, with colony activity remaining approximately constant from three to six weeks. Further, in certain cases, picogram levels of combination cytokines led to higher colony activity than nanogram level supplementation. For example, supplementation with picogram levels of Combination 1 (IL-3/IL-6/SCF) led to total colony content that was 3–6 fold higher than with nanogram levels of Combination 1 (IL-3/IL-6/SCF) at parallel time points.

Figure 9:
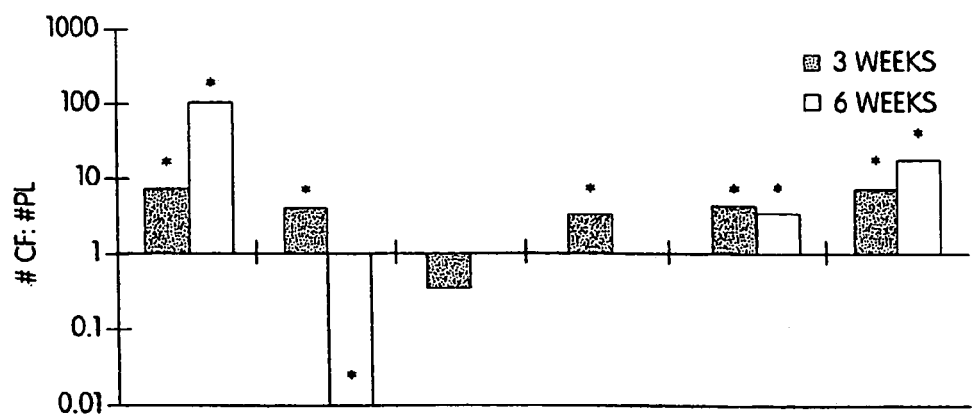
FIG. 9. Fold difference of total colony activity in Cellfoam cultures as compared to plastic control cultures at 3 and 6 weeks in nanogram concentration supplementation experiments.

Analysis of the fold differences in total colony activity between Cellfoam and plastic showed that Cellfoam also generally yielded higher total colony activity as well. With the exception of Combination 2 (IL-3/IL-6/FLK2) at the six week time point, all statistically different colony activity values were in favor of Cellfoam in the nanogram concentration cytokine supplementation trials (FIG. 9). Bars above the 1.00 line indicate the fold higher colony numbers obtained in Cellfoam as compared to controls; bars below the 1.00 line indicate the fold higher numbers obtained in controls as compared to Cellfoam. Scale is shown on log base. Asterisks denote statistically significant values. Picogram concentration supplementation experiments were similar to nanogram levels. Comparison of Cellfoam and BMS cultures yielded similar results.

In summary, the experiments described above indicate that selective use of particular cytokines can lead to the expansion of colony-forming activity as assessed by standard in vitro assays.

All references disclosed herein are incorporated by reference in their entirety.

We claim:

1. A method for in vitro culture of human hematopoietic progenitor cells comprising:
   introducing an amount of hematopoietic progenitor cells into a porous, solid matrix having interconnected pores of a pore size sufficient to permit said cells to grow throughout the matrix, and
   culturing said cells in an environment that is free of inoculated stromal cells, stromal cell conditioned medium, and exogenously added hematopoietic growth factors that promote hematopoietic cell maintenance, expansion and/or differentiation, other than serum, for at least one week with a weekly media change,
   wherein the porous, solid matrix is a unitary microstructure, and wherein the in vitro culture results in an increase in the amount of hematopoietic progenitor cells relative to the amount introduced into said porous, solid matrix.

2. The method of claim 1, wherein the cells are harvested after a one week culture.

3. The method of claim 1, wherein the porous, solid matrix is a metal-coated reticulated open cell foam of carbon containing material.

4. The method of claim 2, wherein the porous, solid matrix is a metal-coated reticulated open cell foam of carbon containing material.

5. The method of claim 3, wherein the metal is tantalum.

6. The method of claim 4, wherein the metal is tantalum.

7. The method of claim 5, wherein the matrix is further coated with fibronectin.

8. The method of claim 6, wherein the matrix is further coated with fibronectin.

9. The method of claim 5, wherein the hematopoietic progenitor cells are CD34+ cells.

10. The method of claim 6, wherein the hematopoietic progenitor cells are CD34+ cells.

11. The method of claim 1, wherein the environment is free of interleukins 3, 6 and 11, stem cell ligand and FLT/FLK ligand growth factors.

12. The method of claim 1, wherein the environment is free of hematopoietic growth factors.

13. The method of claim 1, further comprising after said culturing step, harvesting hematopoietic cells.

14. The method of claim 1, wherein the porous, solid matrix is an open cell porous matrix having a percent open space of at least 75%.

15. The method of claim 1, wherein the porous, solid matrix has pores defined by interconnecting ligaments having a diameter at midpoint, on average, of less than 150 µm.

16. A method for in vitro culture of human hematopoietic progenitor cells comprising:
   introducing an amount of hematopoietic progenitor cells into a porous, solid matrix having interconnected pores of a pore size sufficient to permit said cells to grow throughout the matrix,
   culturing said cells in an environment that is free of inoculated stromal cells, stromal cell conditioned medium, and exogenously added hematopoietic growth factors that promote hematopoietic cell maintenance, expansion and/or differentiation, other than serum, for one week without a media change, and
   harvesting cells,
   wherein the porous, solid matrix is a unitary microstructure,
   wherein the porous, solid matrix is coated with tantalum and fibronectin, and
   wherein the hematopoietic progenitor cells are CD34+ cells.

17. The method of claim 16, wherein the environment is free of interleukins 3, 6 and 11, stem cell ligand and FLT/FLK ligand growth factors.

18. The method of claim 16, wherein the environment is free of hematopoietic growth factors.

19. The method of claim 16, wherein the porous, solid matrix is an open cell porous matrix having a percent open space of at least 75%.

20. The method of claim 16, wherein the porous, solid matrix has pores defined by interconnecting ligaments having a diameter at midpoint, on average, of less than 150 µm.

* * * * *

UNITED STATES PATENT AND TRADEMARK OFFICE
CERTIFICATE OF CORRECTION

| | | |
|---|---|---|
| PATENT NO. | : 7,067,316 B2 | Page 1 of 1 |
| APPLICATION NO. | : 10/705720 | |
| DATED | : June 27, 2006 | |
| INVENTOR(S) | : Mark J. Pykett et al. | |

It is certified that error appears in the above-identified patent and that said Letters Patent is hereby corrected as shown below:

TITLE PAGE, ITEM (57), in line 2 of the abstract, please delete "in vitroculture" and replace with -- *in vitro* culture --.

Signed and Sealed this

Tenth Day of October, 2006

JON W. DUDAS
*Director of the United States Patent and Trademark Office*